US005608073A

United States Patent [19]

Tsujihara et al.

[11] Patent Number: 5,608,073

[45] Date of Patent: Mar. 4, 1997

[54] BACCATIN DERIVATIVES AND PROCESSES FOR PREPARING THE SAME

[75] Inventors: Kenji Tsujihara, Urawa; Tomiki Hashiyama, Saitama; Motoaki Ohashi, Koganei; Noriyuki Nakanishi, Kawaguchi, all of Japan

[73] Assignee: Tanabe Seiyaku Co., Ltd., Osaka, Japan

[21] Appl. No.: 673,580

[22] Filed: Jul. 1, 1996

Related U.S. Application Data

[62] Division of Ser. No. 558,772, Nov. 15, 1995.

[30] Foreign Application Priority Data

| | | | |
|---|---|---|---|
| Nov. 17, 1994 | [JP] | Japan | 5-283780 |
| Sep. 28, 1995 | [JP] | Japan | 6-251185 |

[51] Int. Cl.$^6$ .......... C07D 263/04

[52] U.S. Cl. .......... 548/215

[58] Field of Search .......... 548/215

[56] References Cited

U.S. PATENT DOCUMENTS

| | | | |
|---|---|---|---|
| H1,487 | 9/1995 | Wong et al. . | |
| 4,924,012 | 5/1990 | Colin et al. | 549/510 |
| 4,960,790 | 10/1990 | Stella et al. | 514/449 |
| 5,059,699 | 10/1991 | Kingston et al. | 549/511 |
| 5,254,580 | 10/1993 | Chen et al. | 514/449 |
| 5,283,253 | 2/1994 | Holton et al. | 514/444 |
| 5,284,865 | 2/1994 | Holton et al. | 514/449 |
| 5,352,805 | 10/1994 | Kingston et al. | 549/510 |
| 5,352,806 | 10/1994 | Gunawardana et al. | 549/510 |
| 5,453,520 | 9/1995 | Bombardelli et al. | 549/510 |

FOREIGN PATENT DOCUMENTS

| | | |
|---|---|---|
| 0336841 | 10/1989 | European Pat. Off. . |
| 0473326 | 3/1992 | European Pat. Off. . |
| 0590267 | 4/1994 | European Pat. Off. . |
| 0604910 | 7/1994 | European Pat. Off. . |
| 0624377 | 11/1994 | European Pat. Off. . |
| 0629701 | 12/1994 | European Pat. Off. . |
| 0639577 | 2/1995 | European Pat. Off. . |
| 0671399 | 9/1995 | European Pat. Off. . |
| 60-013776 | 1/1985 | Japan . |
| 60-013775 | 1/1985 | Japan . |
| 94051689 | 2/1988 | Japan . |
| 130577 | 12/1989 | Japan . |
| 3015398 | 1/1991 | Japan . |
| 60-01782 | 1/1994 | Japan . |
| 94004607 | 1/1994 | Japan . |
| 65-04771 | 6/1994 | Japan . |
| 61782 | 11/1994 | Japan . |
| WO90/10443 | 9/1990 | WIPO . |
| WO93/06079 | 4/1993 | WIPO . |
| WO93/10076 | 5/1993 | WIPO . |
| WO94/00156 | 1/1994 | WIPO . |
| WO95/13271 | 5/1994 | WIPO . |
| WO94/10997 | 5/1994 | WIPO . |
| WO94/14787 | 7/1994 | WIPO . |
| WO94/15599 | 7/1994 | WIPO . |
| WO94/15929 | 7/1994 | WIPO . |
| WO94/17050 | 8/1994 | WIPO . |
| WO94/17051 | 8/1994 | WIPO . |
| WO94/17052 | 8/1994 | WIPO . |
| WO94/18186 | 8/1994 | WIPO . |
| WO94/18164 | 8/1994 | WIPO . |
| WO94/20485 | 9/1994 | WIPO . |
| WO94/21250 | 9/1994 | WIPO . |
| WO94/21251 | 9/1994 | WIPO . |
| WO94/21623 | 9/1994 | WIPO . |
| WO94/21651 | 9/1994 | WIPO . |
| WO94/20088 | 9/1994 | WIPO . |
| WO95/04154 | 2/1995 | WIPO . |
| WO95/03265 | 2/1995 | WIPO . |
| WO95/11247 | 4/1995 | WIPO . |
| WO95/20582 | 8/1995 | WIPO . |
| WO95/25728 | 9/1995 | WIPO . |

OTHER PUBLICATIONS

Dictionary of Organic Compounds, p. 506. (1969).
Derwent Abstract EP 253738 (Jan. 20, 1988).
Derwent Abstract of JP 60013775. (Jan. 24, 1985).
Derwent Abstract of JP 60013776. (Jan. 24, 1985).
Derwent Abstract of EP 362556. (Nov. 02, 1994).

(List continued on next page.)

*Primary Examiner*—Johann Richter
*Assistant Examiner*—Jane C. Oswecki
*Attorney, Agent, or Firm*—Finnegan, Henderson, Farabow, Garrett & Dunner, L.L.P.

[57] ABSTRACT

A compound represented by the formula [I]:

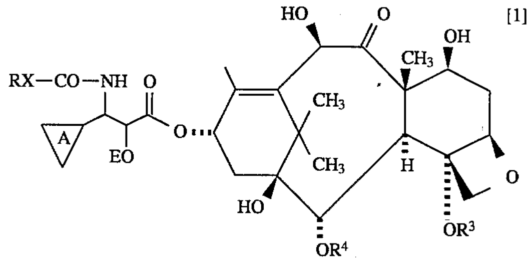

[I]

wherein $R^3$ represents a lower alkanoyl group; $R^4$ represents a substituted or unsubstituted benzoyl group; ring A represents a substituted or unsubstituted cyclopropane ring; X represents a single bond or a group represented by —O—, —S— or —NH—, R represents a substituted or unsubstituted lower alkyl group (wherein said lower alkyl group may have a cycloalkyl moiety), a substituted or unsubstituted aryl group or a substituted or unsubstituted aromatic heterocyclic group; E represents hydrogen atom or a group represented by $—CO(CH_2)_nZY$; Y represents a residue obtained from an amino acid or a dipeptide by removing hydroxyl group in one carboxyl group therefrom (wherein amino group existing in said residue may be protected, and carboxyl group existing in said residue may be esterified or amidated); Z represents a group represented by the formula of —O— or —NH—; and n represents 1, 2, 3, 4, 5 or 6, or a pharmaceutically acceptable salt thereof. Said compounds have excellent antitumor activity so that they are useful in the prophylaxis or treatment of a wide range of tumors such as breast cancer, ovary cancer, lung cancer, malignant melanoma and the like.

2 Claims, No Drawings

OTHER PUBLICATIONS

Derwent Abstract of EP 558623. (Jun. 11, 1992).
Derwent Abstract of EP 336841. (Oct. 11, 1989).
Derwent Abstract of EP 558959 (Sep. 8, 1993).
Chemical Abstract, vol. 110, No. 19, May 8, 1989, Abstract No. 173488h.
"Synthesis and Structure–Activity Relationships of New Antitumor Taxoids," Ojima, Iwao et al., J. Med. Chem. 37(6), pp. 2602–2608 (1994).
M. Suffness, "Chapter 32. Taxol: From Discovery To Therapeutic Use" Annual Reports in Medicinal Chemistry, vol. 28, pp. 305–314 (1993).
J. N. Denis et al., "A Highly Efficient, Practial Approach to Natural Taxol," J. Am. Chem. Soc., vol. 110, pp. 5917–5919 (1988).
U.S. 5,272,171 (Dec. 21, 1993).
A Commercon et al., "Improved Protection and Esterification of a Precursor of the Taxotere® and Taxol Side Chains, "Tetrahedron Letters, vol. 33, No. 36, pp. 5185–5188 (1992).
U.S. Pat. No. 4,184,470 (Jan. 22, 1980).
J. N. Denis et al., "An Efficient, Enantioselective Synthesis of the Taxol Side Chain," J. Org. Chem., vol. 51, pp. 46–50 (1986).
K. C. Nicolaou et al., "Design Synthesis and Biological Activity of Protaxois," Nature, vol. 364, pp. 464–466, (Jul. 29, 1993).
L. Mangatal et al., "Application of the Vicinal Oxyamination Reaction With Asymmetric Induction to the Hemisynthesis of Taxol and Analogues," Tetrahedron, vol. 45, No. 13, pp. 4177–4190 (1989).
J. N. Denis et al., "An Improved Synthesis of the Taxol Side Chain and of RP 56976," J. Org. Chem., vol. 55, pp. 1957–1959 (1990).
U.S. Pat. No. 4,184,470 (Jan. 22, 1980).
I. Ojima et al., "Synthesis and Biological Activity of 3'–alkyl–and 3'–alkenyl–3'–dephenyldocetaxels," Bioorganic & Medicinal Chemistry Letters, vol. 4, No. 21, pp. 2631–2634 (1994).
D. Gou et al., "A Practical Chemoenzymatic Synthesis of the Taxol C–13 Side Chain N–Benzoyl–(2R, 3S)–3–phenylisoserine," J. Org. Chem., vol. 58, pp. 1287–1289 (1993).
T. C. Boge et al., "The Effect of the Aromatic Rings of Taxol on Biological Activity and Solution Conformation: Synthesis and Evaluation of Saturated Taxol and Taxotere Analogues," J. Med. Chem., vol. 37, pp. 3337–3343 (1994).
A. Mori et al., "Asymmetric Simmons–Smith Reactions Using Homochiral Protecting Groups," Tetrahedron, vol. 42, No. 23, pp. 6447–6458 (1986).
L. Li et al., "Synthesis and Biological Evaluation of C–3'–Modified Analogs of 9 (R)–Dihydrotaxol," J. Med. Chem., vol. 37, pp. 2655–2663 (1994).
I. Ojima et al., "Synthesis and Structure–Activity Relationships of New Antitumor Taxoids, Effects of Cyclohexyl Substitution at the C–3' and/or C–2 of Taxotere (Docetaxel)", J. Med. Chem., vol. 37, pp. 2602–2608 (1994).

BACCATIN DERIVATIVES AND PROCESSES FOR PREPARING THE SAME

This application is a division of application Ser. No. 08/558,772, filed Nov. 15, 1995, which is entirely incorporated herein by reference.

TECHNICAL FIELD

The present invention relates to a novel baccatin derivative having an antitumor activity, and processes for preparing the same.

PRIOR ART

It has been known that taxol [4α,10β-diacetoxy-13α-[(2R,3S)-3-benzoylamino-2-hydroxy-3-phenylpropionyloxy]-2α-benzoyloxy-5β,20-epoxy-1β,7β-dihydroxytax-11-en-9-one] is diterpenoide obtained from *Taxus brevifolia*, and has an excellent antitumor activity on various kinds of cancers, but its water-solubility is extremely low, i.e. 0.004 mg/ml or less [Nature, Vol. 346, p. 464 (1993)], which is a clinical problem.

In order to improve the antitumor activity of taxol, the modification of hydroxyl group at 10-position thereof and/or amino group in a side chain at 13-position thereof have been reported [e.g., Japanese Provisional Patent Publications Nos. 30478/1988 and 30479/1988, Tetrahedron Letters, Vol. 33, p. 5185 (1992) and Tetrahedron, Vol. 45, p. 4177 (1989) etc.]. Examples which improve the water-solubility of taxol by modifying hydroxyl group in a side chain at 13-position and/or hydroxyl group at 7-position thereof with a hydrophilic group are disclosed in U.S. Pat. Nos. 4,960,790, 5,059,699, and 5,283,253, and Japanese Provisional Patent Publication No. 1782/1994. U.S. Pat. No. 4,960,790 discloses taxol derivatives obtained by modifying hydroxyl group in a side chain at 13-position thereof and/or hydroxyl group at 7-position thereof directly with the residues obtained from amino acids such as alanine, leucine, isoleucine, and the like. There have been described taxol derivatives obtained by modifying hydroxyl group in a side chain at 13-position thereof with a group such as —CO—$(CH_y)_m$—CO—NH—$(CH_2)_2$—$SO_3$—M (wherein y is 1 or 2, m is 1 to 3, M is hydrogen atom, an alkali metal atom, and the like, e.g., sodium 4-(2-sulfonatoethyl)amino-1,4-dioxobutyl group) in U.S. Pat. No. 5,059,699. In Japanese Provisional Patent Publication No. 1782/1994, there have been described taxol derivatives obtained by esterifing hydroxyl group in a side chain at 13-position, hydroxyl group at 7-position, and/or hydroxyl group at 10-position thereof with phosphoric acid or carbonic acid. Furthermore, in U.S. Pat. No. 5,283,253, taxol derivatives obtained by modifying amino group in a side chain at 13-position thereof with furancarbonyl group or thiophenecarbonyl group and hydroxyl group in a side chain at 13-position and/or hydroxyl group at 7-position thereof with a carboxyl group-substituted or carbamoyl group-substituted lower alkanoyl group and the like are disclosed. Meanwhile, WO 94-10997 discloses a taxol derivative, which is obtained by replacing phenyl group in a side chain at 13-position thereof by cyclopropyl group, and has acetoxy group at 10-position.

However, heretofore, it has not been reported that a taxol derivative having high water-solubility, stability, and excellent antitumor activity is used clinically.

BRIEF DESCRIPTION OF INVENTION

An object of the present invention is to provide novel baccatin derivatives having an excellent antitumor activity, and novel baccatin derivatives having an excellent antitumor activity and an improved water-solubility. Still another object of the present invention is to provide processes for preparing such novel baccatin derivatives.

DETAILED DESCRIPTION OF INVENTION

The present invention relates to a compound represented by the formula [I]:

[I]

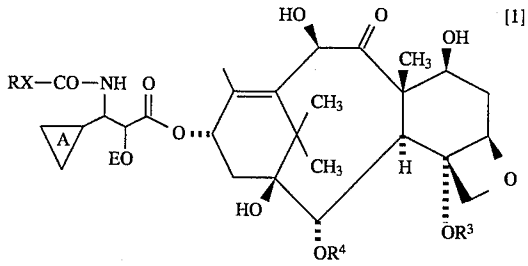

wherein $R^3$ represents a lower alkanoyl group; $R^4$ represents a substituted or unsubstituted benzoyl group; ring A represents a substituted or unsubstituted cyclopropane ring; X represents a single bond or a group represented by —O—, —S— or —NH—; R represents a substituted or unsubstituted lower alkyl group (wherein said lower alkyl group may have a cycloalkyl moiety), a substituted or unsubstituted aryl group or a substituted or unsubstituted aromatic heterocyclic group; E represents hydrogen atom or a group represented by —$CO(CH_2)_n$ZY; Y represents a residue obtained from an amino acid or a dipeptide by removing hydroxyl group in one carboxyl group therefrom (wherein amino group existing in said residue may be protected, and carboxyl group existing in said residue may be esterified or amidated); Z represents a group represented by the formula of —O— or —NH—; and n represents 1, 2, 3, 4, 5 or 6, or a pharmaceutically acceptable salt thereof.

In the desired compound [I], as the substituent on ring A, there may be mentioned a halogen atom, a lower alkyl group, a lower alkoxy group, and the like.

As a substituent on benzoyl group of $R^4$, there may be mentioned a lower alkyl group, a lower alkoxy group, a halogen atom, and the like.

As a substituent on a lower alkyl group, an aryl group, or an aromatic heterocyclic group of R, there may be mentioned a halogen atom, a lower alkoxy group, and the like. As an aryl group, there may be mentioned an aromatic hydrocarbocyclic group such as phenyl group, naphtyl group, and the like. As an aromatic heterocyclic group, there may be mentioned an aromatic heteromonocyclic group having sulfur atom, oxygen atom, and/or nitrogen atom as a hetero atom, for example, a 5- or 6-membered aromatic heterocyclic group such as thienyl group, furyl group, pyridyl group, pirazinyl group, pyrimidinyl group, and the like. As the lower alkyl group having a cycloalkyl moiety, there may be mentioned, for example, cyclopropylmethyl group, cyclobutylmethyl group, (2,2-dimethyl-cyclopropyl-)methyl group, and the like. Further, as an example of the lower alkyl group having a substituent and also having a cycloalkyl moiety, there may be mentioned (2,2-difluoro-3,3-dimethylcyclopropyl)methyl group and the like.

In the desired compound [I], when E is a group represented by —$CO(CH_2)_n$ZY, the amino acids corresponding to the residue Y includes amino acids natural or non-natural sources and are the compounds having at least one amino group and one carboxyl group in a molecule. Those amino acids include amino acids from natural sources or antipodes thereof, D- or L-synthetic amino acids, and racemic mixtures of these amino acids.

α-Amino acids or β-amino acids are the preferred examples and may be either one of neutral, acidic, and basic amino acids. As the basic amino acids, there may be mentioned amino acids having plural amino groups such as asparagine, ornithine, lysine, and the like; as the acidic amino acids, there may be mentioned amino acids having plural carboxyl groups such as glutamic acid, aspartic acid, and the like; and as the neutral amino acids, there may be mentioned amino acids having the same number of amino groups and carboxyl groups such as alanine, isoleucine, leucine, and the like. Further, in the present invention, specific examples of the amino acids which can be used suitably, include glycine, alanine, isoleucine, leucine, valine, glutamic acid, methionine, phenylalanine, proline, β-alanine, arginine, ornithine, serine, threonine, asparagine, aspartic acid, glutamine, cystine, cysteine, tyrosine, histidine, tryptophan, lysine, sarcosine, creatine, homocysteine, norleucine, isoserine, homoserine, norvaline, ε-aminocaproic acid, thioproline, α-aminoisobutanoic acid, piperidylcarboxylic acid, α,γ-diaminobutyric acid, β-aminobutyric acid, γ-aminobutyric acid, and the like.

Furthermore, a dipeptide consisting of the above-mentioned amino acid may be used as the peptide of Y. Dipeptides consisting the above-mentioned natural amino acids or antipodes thereof such as glycylglycine, valylglycine, methionylglycine, prolylglycine, glycylproline, phenylalanylglycine, glycylvaline, alanylproline, valylproline, phenylalanylvaline, and the like are the examples thereof.

When the amino group in Y is protected, a conventional protecting group may be used for the protection of Y. For example, there may be mentioned benzyloxycarbonyl group, tert-butoxycarbonyl group, a lower alkyl group, and the like as the protecting groups. When the carboxyl group in Y is esterified, as the ester residue, for example, there may be a lower alkyl group such as methyl group, ethyl group, and the like, or a lower alkoxy-lower alkyl group such as methoxyethyl group, methoxyethoxyethyl group, and the like.

As a preferred example of the desired compound [I]in the present invention, there may be mentioned a compound in which E is a group represented by $-CO(CH_2)_nZY$.

As a more preferred example of the desired compound [I], there may be mentioned a compound in which Y is a residue obtained from an α- or β-amino acid, or a dipeptide consisting of these amino acids by removing hydroxyl group in one carboxyl group therefrom (wherein amino group existing in said residue may be protected, and carboxyl group existing in said residue may be esterified, or amidated).

As a further preferred compound of the desired compound [I] in the present invention, there may be mentioned a compound in which ring A is a cyclopropane ring which may be substituted with 1 or 2 groups selected from the groups consisting of a halogen atom, a lower alkyl group, and a lower alkoxy group; R is a lower alkyl group which may be substituted with 1 to 3 groups selected from the groups consisting of a halogen atom and a lower alkoxy group (wherein said lower alkyl group may have a 3- to 5-membered cycloalkyl moiety), a phenyl group which may be substituted with 1 or 2 lower alkoxy groups, furyl group, or thienyl group; and Y is a residue obtained from a natural amino acid or an antipode thereof or a dipeptide consisting of a natural amino acid or an antipode thereof by removing hydroxyl group in one carboxyl group therefrom (wherein amino group existing in said residue may be protected with benzyloxycarbonyl group or a lower alkyl group, and carboxyl group existing in said residue may be esterified with a lower alkyl group which may be substituted with a lower alkoxy group, or amidated).

As most preferred compound of the desired compound [I], there may be mentioned a compound in which Y is a residue obtained from asparagine, aspartic acid, glutamine, glutamic acid, proline, glycine, alanine, β-alanine, or a dipeptide consisting of these amino acids by removing hydroxyl group in one carboxyl group therefrom (wherein amino group existing in said residue may be protected with benzyloxycarbonyl group or a lower alkyl group, and carboxyl group existing in said residue may be esterified with a lower alkyl group which may be substituted with a lower alkoxy group, or amidated), and a compound in which ring A is cyclopropane ring which may be substituted with a lower alkyl group; R is a lower alkyl group, furyl group or thienyl group; Y is a residue obtained from asparagine, aspartic acid, glutamine, glutamic acid, proline, glycine, or β-alanine by removing hydroxyl group in one carboxyl group therefrom (wherein carboxyl group existing in said residue may be esterified with a lower alkyl group, or amidated) is particularly preferred.

As a compound exhibiting an excellent pharmaceutical effect, there may be mentioned a compound represented by the formula [I] in which $R^3$ is acetyl group, $R^4$ is benzoyl group, X is a group represented —O—; R is a lower alkyl group; and Y is asparaginyl group, aspartyl group, β-alanyl group, or prolyl group (wherein carboxyl group existing in said residue is esterified with a lower alkyl group, or amidated).

As concrete compounds, for example, there may be mentioned compounds shown in Tables 7–7.

TABLE 1

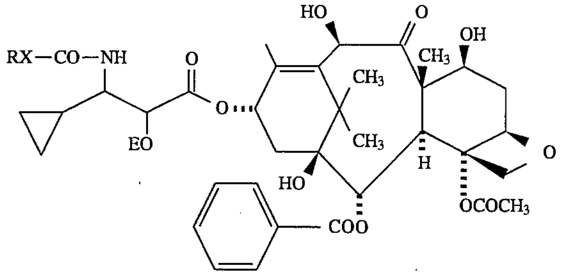

| RX | E |
|---|---|
| $(H_3C)_3CO-$ | 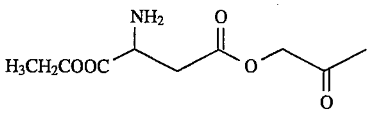 |
| $(H_3C)_3CO-$ | H |
| 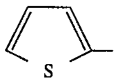 | H |
| $(H_3C)_3CS-$ | H |
| 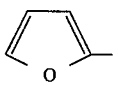 | 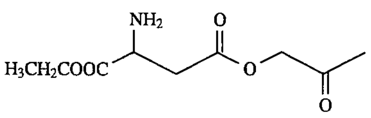 |

TABLE 2
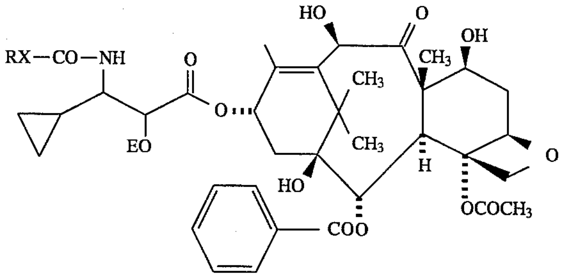
| RX | E |
| --- | --- |
| $H_3C(CH_2)_3-$ | 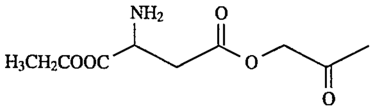 |
| $(H_3C)_3CHN-$ | 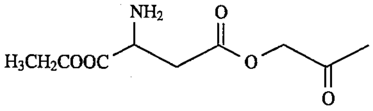 |
| $(H_3C)_3CO-$ | 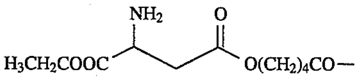 |
| $(H_3C)_3CO-$ | 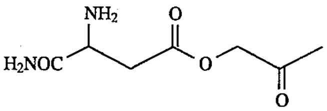 |
TABLE 2-continued
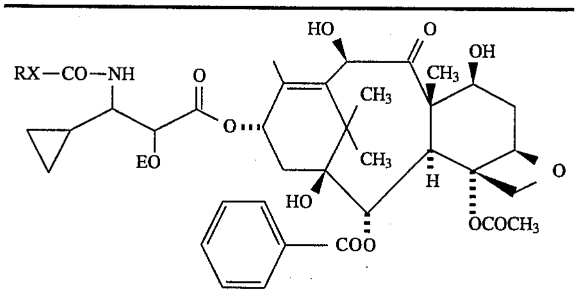
| RX | E |
| --- | --- |
| $(H_3C)_3CO-$ | 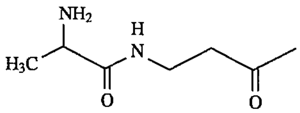 |
| $(H_3C)_3CO-$ | 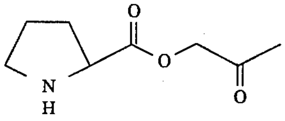 |
TABLE 3
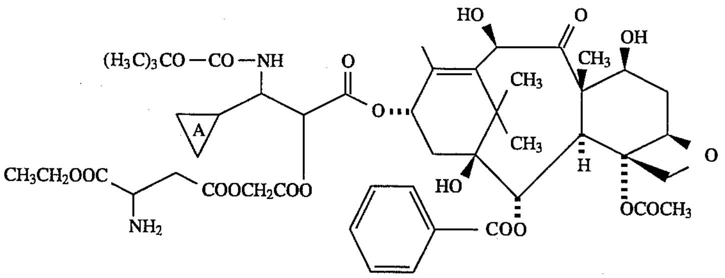
| ring A |
| --- |
| 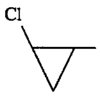 |
| 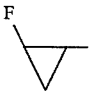 |
| 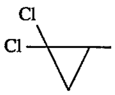 |
| 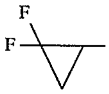 |

TABLE 3-continued
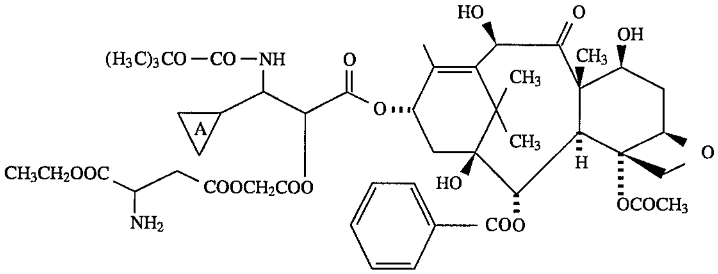
ring A
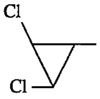
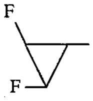
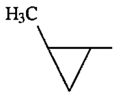
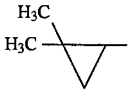
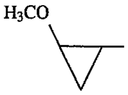
TABLE 4
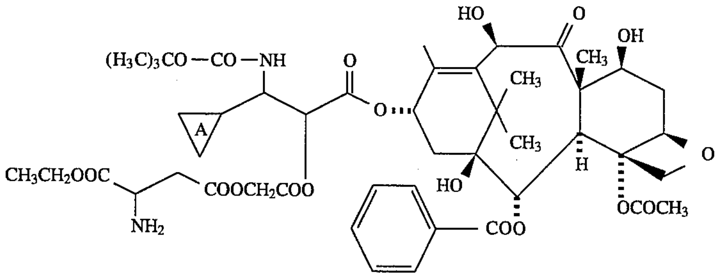
ring A
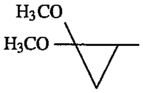
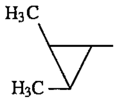

TABLE 4-continued
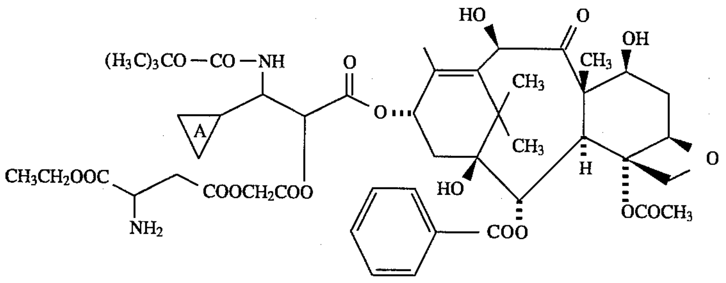
| ring A |
|---|
| 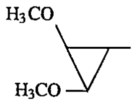 |
| 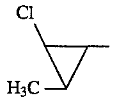 |
| 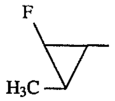 |
| 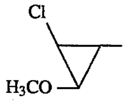 |
| 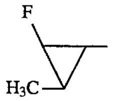 |
| 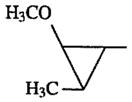 |
TABLE 5
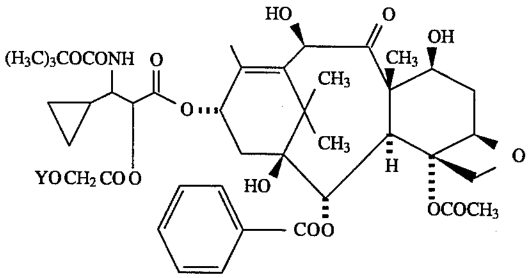
| Y* |
|---|
| Glycyl |
| Alanyl |
| Isoleucyl |
| Leucyl |
| Valyl |
| α-Glutamyl |
| γ-Glutamyl |
| Methionyl |
| Phenylalanyl |
TABLE 5-continued
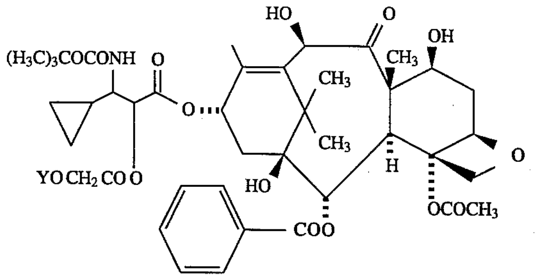
| Y* |
|---|
| β-Alanyl |
| Arginyl |
| Ornithyl |
| Seryl |
| Threonyl |
| Asparaginyl |
*: amino group and/or carboxyl group in Y may be protected.

TABLE 6

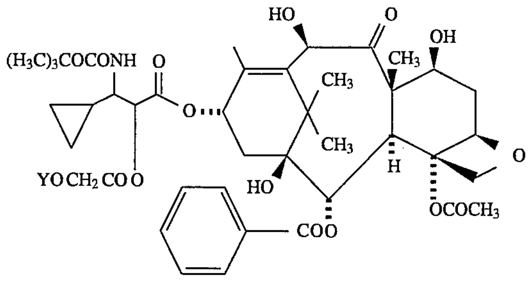

| Y* |
|---|
| α-Aspartyl |
| β-Aspartyl |
| Glutaminyl |
| Cystyl |
| Cysteinyl |
| Tyrosyl |
| Histidyl |
| Tryptophyl |
| Lysyl |
| Sarcosyl |
| Creatinyl |
| Homocysteinyl |
| Norleucyl |
| Isoseryl |
| Homoseryl |
| Norvalyl |

*: amino group and/or carboxyl group in Y may be protected.

TABLE 7

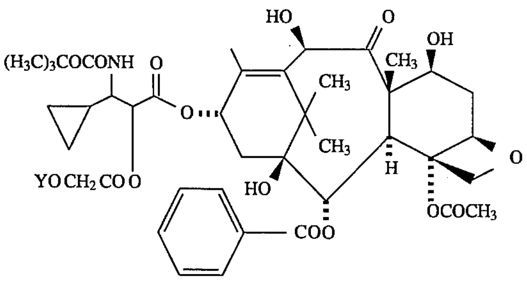

| Y* |
|---|
| ε-aminocapronyl |
| Thioprolyl |
| α-aminoisobutanoyl |
| piperidylcarbonyl |
| α,γ-diaminobutylyl |
| β-aminobutylyl |
| γ-aminobutylyl |
| glycylglycyl |
| valylglycyl |
| methionylglycyl |
| prolylglycyl |
| glycylprolyl |
| glycylphenylalanyl |
| glycylvalyl |
| alanylprolyl |
| valylprolyl |
| phenylalanylvalyl |

*: amino group and/or carboxyl group in Y may be protected.

In the desired compound [I] in the present invention, various stereo isomers and optical isomers based on two asymmetric carbon atoms of a substituted 3-cyclopropylpropionyloxy group bonded to a carbon atom at 13-position of a taxane skeleton and an asymmetric carbon atom existing in a substituent thereof can exist. All of these stereoisomers, optical isomers, and mixtures thereof are included in the present invention.

The desired compound [I] in the present invention can be used for medicinal purpose either in a free form or in the form of pharmaceutically acceptable salts thereof. As the pharmaceutically acceptable salts, there may be mentioned acid addition salts with inorganic acids or organic acids such as hydrochloride, sulfate, nitrate, hydrobromide, methanesulfonate, toluenesulfonate, acetate, and the like.

The desired compound [I] in the present invention or pharmaceutically acceptable salts thereof can be administered either orally or parenterally, and it can be used as a suitable pharmaceutical preparation, for example, a tablet, a granule, a capsule, a powder, an injection, and an inhalation by the conventional process.

The dose of the desired compound [I] in the present invention or a pharmaceutically acceptable salt thereof varies depending on an administration method, age, body weight, and state of a patient, but, in general, the daily dose is preferably about 5 to 200 $mg/m^2$, particularly preferably 20 to 150 $mg/m^2$.

According to the present invention, the desired compound [I] can be prepared:

(1) by reacting a compound represented by the formula [II]:

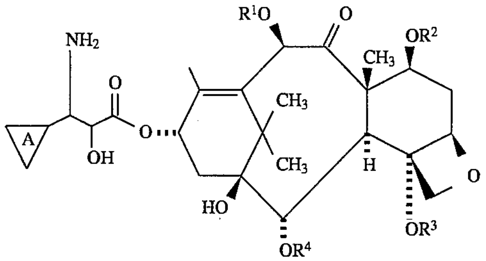

[II]

wherein $R^1$ represents a protecting group of hydroxyl group; $R^2$ represents a protecting group of hydroxyl group; $R^3$, $R^4$, and ring A are the same as defined above, or a salt thereof with a compound represented by the formula [III]:

RX—COOH [III]

wherein R and X is the same as defined above, a salt thereof, or a reactive derivative thereof to obtain a compound represented by the formula [V]:

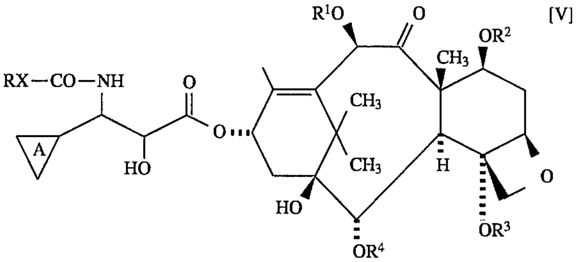

[V]

wherein $R^1$, $R^2$, $R^3$, $R^4$, ring A, X, and R are the same as defined above, and removing the protecting groups of the hydroxyl groups at 7-position and 10-position in the compound;

(2) by reacting the compound [II] or a salt thereof with the compound [III], a salt thereof, or a reactive derivative thereof, to obtain the compound [V], reacting the compound [V] with a compound represented by a formula [IV]:

E'OH [IV]

wherein E' is a group represented by $-CO(CH_2)_nZY$; Y, Z, and n are the same as defined above, a salt thereof, or a reactive derivative thereof, and removing the protecting groups of the hydroxyl groups at 7-position and 10-position in the obtained compound; or (3) by reacting the compound [II] or a salt thereof with the compound [III], a salt thereof, or a reactive derivative thereof, to obtain the compound [V], removing the protecting groups of the hydroxyl groups at 7-position and 10-position in the compound [V], and then reacting the resulting compound with the formula [IV], a salt thereof, or a reactive derivative thereof.

In the process described above, by the reaction of the compound [II] or a salt thereof with the compound [III], a salt thereof, or a reactive derivative, the compound [V] can be prepared. By the reaction of the compound [V] with the compound [IV], a salt thereof, or a reactive derivative thereof, the removal of the protecting group of the hydroxyl group in the resulting compound, and if necessary, the removal of the protecting group of amino group and the ester residue of carboxyl group, a compound represented by the formula [I-a]:

[I-a]

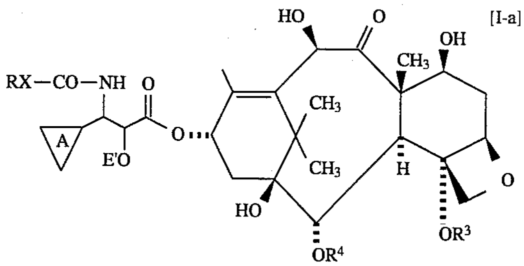

wherein $R^1$, $R^2$, $R^3$, $R^4$, ring A, X, R, and E' are the same as defined above, can be prepared.

Also, according to the present invention, the compound [I-a] can be prepared by:

(a) reacting the compound [II] or a salt thereof with the compound [III], a salt thereof, or a reactive compound to obtain the compound [V];

(b) reacting the compound [V] with a compound represented by the formula [VI]:

$R^5Z(CH_2)_nCOOH$ [VI]

wherein $R^5$ represents a protecting group of hydroxyl group or amino group, Z and n are the same as defined above, a salt thereof, or a reactive derivative thereof;

(c) removing the protecting group $R^5$ from the obtained compound to obtain a compound represented by the formula [VII]:

[VII]

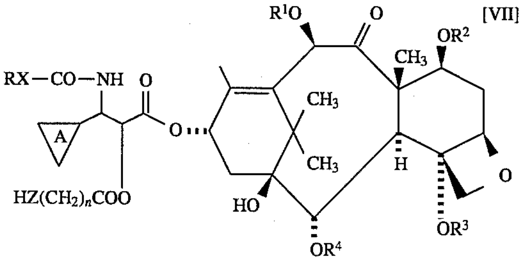

wherein $R^1$, $R^2$, $R^3$, $R^4$ ring A, X, R, Z, and n are the same as defined above;

(d) reacting the compound [VII] with a compound represented by the formula [VIII]:

YOH [VIII]

wherein Y is the same as defined above; and (e) removing the protecting group of hydroxyl group, if necessary, removing the protecting group of amino group and the ester residue of carboxyl group.

Also, according to the present invention, by reacting a compound represented by the formula [IX]:

[IX]

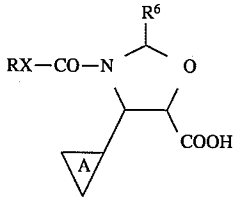

wherein $R^6$ represents a substituted phenyl group, ring A, X, and R are the same as defined above, or a reactive derivative thereof with a compound represented by the formula [X]:

[X]

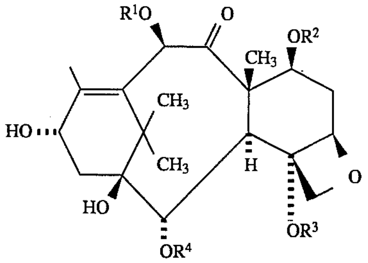

wherein $R^1$,$R^2$,$R^3$ and $R^4$ are the same as defined above, and then subjecting the resulting condensate to the cleavage reaction of an oxazolidine ring to obtain the compound [V], and removing the protecting groups of the hydroxyl groups at 7-position and 10-position in the compound [V], the compound represented by a formula [I-b]:

[I-b]

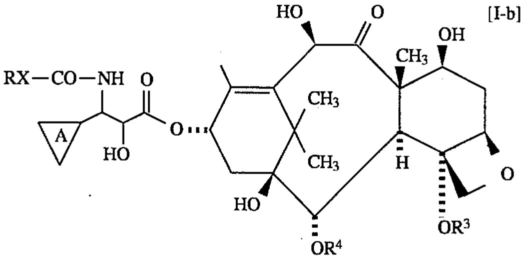

wherein $R^3$, $R^4$, ring A, X, and R are the same as defined above, can be prepared.

In the compound [IX], as the substituent of phenyl group of $R^6$, there may be mentioned electron donating groups, or example, alkoxy group, amino group, and the like.

As the salt of the compound [II], there may be mentioned, for example, organic acid salts such as formate, acetate, methanesulfonate, p-toluenesulfonate, and the like, and inorganic acid salts such as hydrochloride, hydrobromide, and the like.

As the protecting groups $R^1$ and $R^2$ of the hydroxyl groups at 7-position and 10-position in taxane skeleton, there may be mentioned a lower alkanoyl group, 2,2,2-trichloroethoxycarbonyl group, triethylsilyl group, and the like, and these protecting groups $R^1$ and $R^2$ may be different protecting groups. As examples of different protecting groups, there may be mentioned that $R^1$ is 2,2,2-trichloroethoxycarbonyl group and $R^2$ is triethylsilyl group. When the protecting groups in the compound [VI] are the protecting groups of hydroxyl group, there may be mentioned the conventional protecting groups such as benzyl group and the like. On the other hand, when the protecting groups in the compound [VI] are the protecting groups of amino group, there may be mentioned the conventional protecting groups such as benzyloxycarbonyl group and the like.

As the reactive derivatives of the compound [III], the compound [IV] and the compound [VI], there may be mentioned an acid halide, an active ester, a mixed acid anhydride, and the like. As the reactive derivative of the compound [III], there also may be mentioned isocyanate.

When the compound [III], the compound [IV], or the compound [VI] is used in the condensation, the condensing reaction can be carried out in the presence or absence of a dehydrating agent in a suitable solvent or without a solvent. As the dehydrating agent, there may be suitably used dicyclohexylcarbodiimide, carbonyldiimidazole, 1-methyl-2-bromopyridinium iodide and benzotriazol-1-yloxytris(dimethylamino)phosphonium hexafluorophosphate. As the solvent, there may be suitably used dichloromethane, dimethyl ether, dimethylformamide, dioxane, tetrahydrofuran, and toluene. The present reaction proceeds suitably at −20° to 100° C., particularly 0° to 30° C.

On the other hand, when the reactive derivative of the compound [III], the compound [IV], or the compound [VI] is used in the condensation, the condensing reaction can be carried out in the presence or absence of an acid acceptor in a suitable solvent. As the acid acceptor, there may be suitably used an alkali metal hydride, an alkali metal carbonate, an alkali metal hydrogen carbonate, and an organic base (e.g., triethylamine, diisopropylethyl-amine, pyridine, 4-(N,N-dimethylamino)pyridine, and 1,8-diazabiclo [5.4.0] undec-7-ene). As the solvent, there may be suitably used dichloromethane, dimethyl ether, dimethylformamide, dioxane, tetrahydrofuran, and toluene. The present reaction proceeds suitably at −20° to 80° C., particularly 0° to 30° C.

The condensing reaction of the compound [VIII] with the compound [VII] can be carried out in the presence of a dehydrating agent and an acid acceptor in a suitable solvent. As the de hydrating agent, there may be suitably used dicyclohexylcarbodiimide, carbonyldiimidazole, 1-methyl-2-bromopyridinium iodide, and benzotriazol-1-yloxytris-(dimethylamino)phosphoniumhexafluorophosphate. As the acid acceptor, there may be suitably used an alkali metal hydride, an alkali metal carbonate, an alkali metal hydrogen carbonate, and an organic base (e.g., triethylamine, diisopropylethyl-amine, pyridine, 4-(N,N-dimethylamino)pyridine, and 1,8-diazabiclo [5.4.0]undec-7-ene). As the solvent, there may be suitably used dichloromethane, dimethyl ether, dimethylformamide, dioxane, tetrahydrofuran, and toluene. The present reaction proceeds suitably at −20° to 80° C., particularly 0° to 30° C.

The condensing reaction of the compound [IX] or a reactive derivative thereof with the compound [IX] can be carried out in a suitable solvent. As the solvent, there may be suitably used dichloromethane, dimethyl ether, dimethylformamide, dioxane, tetrahydrofuran, and toluene. As the reactive derivative, there may be mentioned an add halide (e.g., acid chloride, acid bromide, and acid iodide), an active ester (e.g., p-nitrophenyl ester), and a mixed acid anhydride [e.g., a mixed acid anhydride with benzoic acid which is substituted with 1–5 group(s) selected from a halogen atom, nitro group, a lower alkyl group, and a lower alkoxy group].

The condensing reaction of the compound [IX] with the compound [X] can be carried out in the presence of a dehydrating agent and an acid acceptor. As the dehydrating agent, there may be suitably used dicyclohexylcarbodiimide, carbonyldiimidazole, 1-methyl-2-bromopyridinium iodide, and benzotriazol-1-yloxytris(dimethylamino)phosphonium hexafluorophosphate. As the acid acceptor, there may be suitably used an organic base (e.g., triethylamine, diisopropylethylamine, pyridine, 4-(N,N-dimethylamino)pyridine, and 1,8-diazabiclo [5.4.0] undec-7-ene). The present reaction proceeds suitably at 0° to 120° C., particularly 10° to 80 ° C.

On the other hand, the condensing reaction of the reactive derivative of the compound [IX] with the compound [IX] can be carried out in the presence or absence of an acid acceptor. As the acid acceptor, there may be used an organic base (e.g., pyridine, triethylamine, N-methylpiperidine, N-methylmorpholine, N,N-diisopropyl-N-ethylamine, 4-(N, N-dimethylamino)pyridine, and 4-pyrrolinopyridine). The reaction proceeds suitably at 0° to 120° C., particularly 10° to 80° C.

The cleavage reaction of an oxazolidine ring can be carried out in the presence of an acid in a suitable solvent. As the acid, there may be used acids such as p-toluenesulfonic acid, camphorsulfonic acid, methanesulfonic acid, hydrochloric acid, and the like. As the solvent, there may be suitably used alcohol, particularly methanol. The present reaction proceeds suitably at −20° to 80° C., particularly 0° to 30° C.

The removal of the protecting groups of the hydroxyl groups at 7-position and 10-position in taxane skeleton can be carried out by a conventional method depending on the kind of protecting groups. For example, when said protecting groups are 2,2,2-trichloroethoxycarbonyl groups, zinc-acetic acid may be used for removing them, and when said protecting groups are triethylsilyl groups, p-toluenesulfonic acid may be used for removing them. The removal of the protecting group $R^5$ from the compound obtained by the reaction of the compound [V] and the compound [VI], a salt thereof, or a reactive derivative thereof can be carried out by a conventional method depending on the kind of protecting group. For example, when said protecting group is benzyl group, palladium-carbon in a suitable solvent (for example, tetrahydrofuran) may be used for removing it. The removal of the protecting group of the amino group at β-position in a side chain at 13-position in the compound [II] can be carried out by a conventional method depending on the kind of protecting group. For example, when said protecting group is benzyloxycarbonyl group, palladium-carbon without a solvent or in suitable solvent (for example, tetrahydrofuran) may be used for removing it.

The compound represented by the formula [II] in the present invention can be prepared by condensing a compound represented by the formula [IX]:

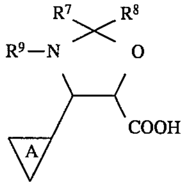

[XI]

wherein $R^7$ and $R^8$ represent lower alkyl groups, $R^9$ represents a protecting group, ring A is the same as defined above, or a reactive derivative thereof with the compound [X] in the same manner as the reaction of the compound [IX] or a reactive derivative thereof with the compound [IX], then subjecting the resulting condensate to the steps of cleaving of an oxazolidine ring and removing the protecting group $R^9$.

In the compound [XI], as the protecting group $R^9$, there may be mentioned the conventional protecting groups such as tert-butoxycarbonyl group and the like.

As the reactive derivative of the compound [XI], there may be mentioned the same reactive derivative of the compound [IX] such as an acid halide, an active ester, and a mixed acid anhydride.

The cleavage reaction of an oxazolidine ring can be carried out in the presence of an acid. As the acid, there may be suitably used formic acid. The present reaction proceeds suitably at 0° to 50° C., particularly 15° to 30° C.

Also, the compound [II] can be prepared by subjecting a compound represented by the formula [XII]:

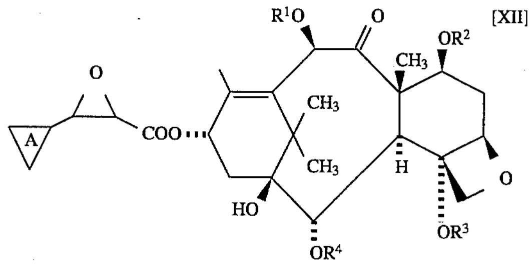

[XII]

wherein $R^1$, $R^2$, $R^3$, $R^4$, and ring A are the same as defined above, to azide-introduction reaction using metal azide to obtain a compound represented by the formula [XIII]:

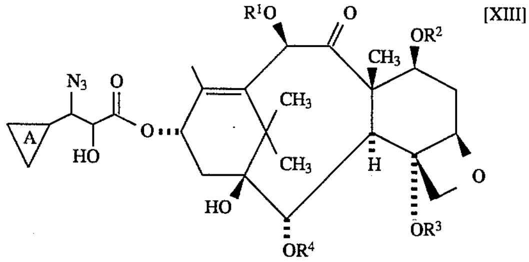

[XIII]

wherein $R^1$, $R^2$, $R^3$, $R^4$, and ring A are the same as defined above, and reducing the azide group of the compound [XIII].

The compound [XI] and the compound [IX] can be prepared, for example, as shown in the following reaction scheme.

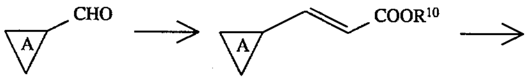

[XXII] [XXI]

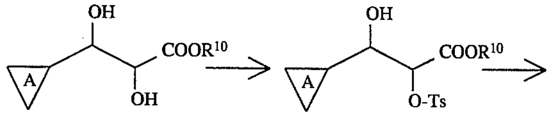

[XX] [XIX]

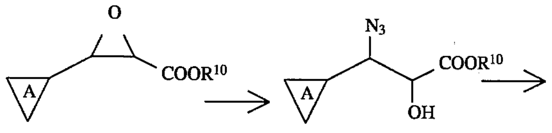

[XVIII] [XVII]

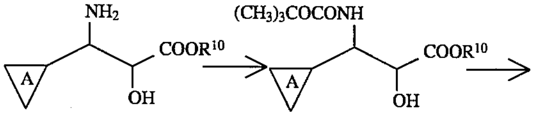

[XVI] [XV]

-continued

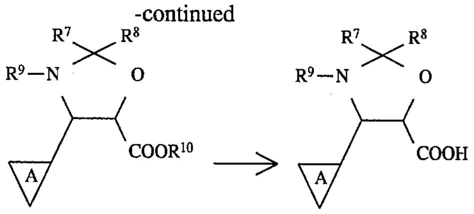

[XIV] [XI]

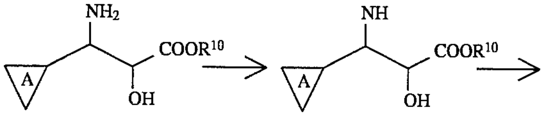

[XVI] [XXIV]

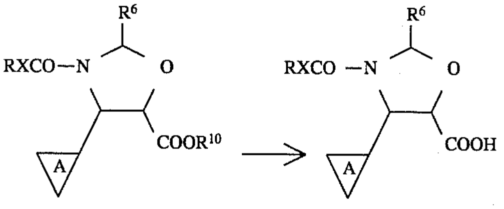

[XXIII] [IX]

wherein $R^{10}$ represents an ester residue; Ts represents p-toluenesulfonyl group; ring A is the same as defined above.

The compound [XI] in which ring A is cyclopropyl group can be prepared by dihydroxylating 3-cyclopropylacrylic acid ester [XXI] to obtain the compound [XX], eliminating hydroxyl group at 2-position to prepare 3-cyclopropyl-2-oxiranecarboxylic acid ester [XVIII], subjecting the compound to the azide-introduction reaction using metal azide to obtain the compound [XVII], subjecting the resulting compound to the reduction reaction to the compound [XVI], protecting amino group with $R^9$ (tert-butoxycarbonyl group) to obtain 3-tert-butoxycarbonylamino-2-hydroxy-3-cyclopropylpropionic acid ester [XV], subjecting the said compound to the oxazolidine ring formation to obtain the compound [XIV], and hydrolysis of the compound [XIV].

The compound [IXII] can be prepared by hydrolysis of the compound [XVIII] to obtain the compound represented by the formula [XXV]:

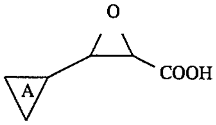

[XXV]

wherein ring A is the same as defined above, reacting the compound [XXV] or a reactive derivative thereof with the compound [X] in the same manner as the reaction of the compound [IX] or a reactive derivative thereof with the compound [X].

As the reactive derivative of the compound [XXV], there may be mentioned the same reactive derivative of the compound [IX] such as an acid halide, an active ester, and a mixed acid anhydride.

The compound [X] can be prepared by protecting hydroxyl groups at 7-position and 10-position in 10-deacetylbaccatin III by the method described in Japanese Provisional Patent Publications Nos. 305077/1988, 30479/1987, and Journal of American Chemical Society, Vol. 1.110, p. 5917, (1998).

The compound [IV] can be prepared by reacting a compound represented by the formula [VIII]:

YOH [VIII]

wherein Y is the same as defined above, or a reactive derivative thereof with a compound represented by the formula [XXVI]:

$HZ(CH_2)_nCOOR^{11}$ [XXVI]

wherein $R^{11}$ represents hydrogen atom or an ester residue; and Z and n are the same as defined above, and removing the ester residue, if necessary.

The compound [XXII] can also be prepared by the hydrolysis of the substituted or unsubstituted cyclopropanecarbaldehyde acetals reported in Tetrahedron, Vol. 42, p. 6447–6458, (1986).

In the present invention, as the lower alkyl group, there may be mentioned, for example, that having 1 to 6 carbon atoms, particularly 1 to 4 carbon atoms such as methyl group, ethyl group, propyl group, isopropyl group, butyl group, isobutyl group, secondary butyl group, tertiary bytyl group, pentyl group, isopentyl group, neopentyl group, tertiary pentyl group, and hexyl group. As the lower alkanoyl group, there may be mentioned, for example, that having 2 to 7 carbon atoms, particularly 2 to 5 carbon atoms such as acetyl group, propionyl group, butyryl group, valeryl group, and pivaloyl group. As the halogen atom, there may be mentioned chlorine, bromine, fluorine, and iodine.

In the present specification, the taxane or taxane skeleton represents a diterpene skeleton represented by the following formula.

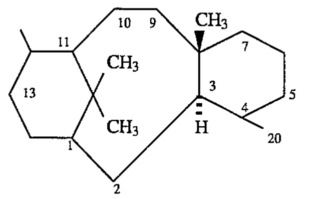

EXAMPLES

The present invention is illustrated in more detail by the following Examples, but should not be construed to be limited thereto.

Example 1

(1) To a suspension of 85.8 g of methoxycarbonylmethylenetriphenylphosphorane in 550 ml of benzene is added dropwise a solution of 15.0 g of cyclopropanecarbaldehyde in 50 ml of benzene at room temperature under argon atmosphere. The mixture is stirred at 55° C. overnight. After the reaction mixture is cooled to room temperature, the reaction mixture is poured into 800ml of ice water. The aqueous mixture is extracted with 600 ml of chloroform twice. The chloroform layer is washed with brine. The organic layer is dried and evaporated under reduced pressure to remove the solvent. The residue is purified by silica gel column chromatography (solvent; hexane:ethyl acetate=12:1) to give 17.4 g of methyl trans-3-cyclopropylacrylate.

Yield: 65%

MS(m/z): 126($M^+$)

IR(neat,$cm^{-1}$): 1720,1660

NMR($CDCl_3$, δ): 0.60–0.68(2H,m), 0.91–0.99(2H,m), 1.51–1.64(1H,m), 3.71(3H,s), 5.90(1H,d,J=15 Hz), 6.43(1H,dd,J=10,15 Hz)

(2)To a solution of 68.2 g of potassium ferricyanide and 28.6 g of potassium carbonate in 640 ml of tert-butanol-water (1:1) is added 0.537 g of 1,4-bis(9-O-dihydroquinidyl)phthalazine. The pH of the reaction mixture is adjusted to pH 10.9 with aqueous solution of phosphoric acid. After a solution of osmium tetroxide in 0.35 ml of toluene (0.393M) is added to the mixture, the resulting mixture is stirred at room temperature for 30 minutes. Then, methyl trans-3-cyclopropylacrylate is added to the mixture, and the mixture is stirred for 24 hours. After the reaction mixture is cooled with ice, 106 g of sodium sulfite is added to the mixture. Then, the mixture is stirred for 30 minutes. The mixture is extracted with ethyl acetate four times. The organic layer is dried and the solvent is removed in vacuo. The residue is purified by silica gel column chromatography (solvent; hexane:ethyl acetate=3:1) to give 4.22 g of methyl (2S,3R)-3-cyclopropyl-2,3-dihydroxypropionate.

Yield: 38% m.p.: 54°–57° C. $[\alpha]_D^{20}$+42.7° (c=1,chloroform) FAB-MS(m/z): 183($M^+$+Na) IR(nujol,$cm^{-1}$): 3440,1730

NMR($CDCl_3$, δ): 0.25–0.34(1H,m), 0.38–0.47(1H,m), 0.52–0.69(2H,m), 1.15–128(1H,m), 2.24(1H, d,J=7 Hz), 3.12(1H, ddd,J=2,7,9 Hz), 3.18(1H, d,J=6 Hz), 4.25(1H,dd, J=2,6 Hz).

(3) Under argon atmosphere, a solution of 4.22 g of methyl (2S,3R)-3-cyclopropyl-2,3-dihydroxypropionate in 140 ml of methylene chloride is cooled to −3° C. Then, 4.00 g of triethylamine and 5.17 g of p-toluenesulfonyl chloride are added to the mixture successively. The mixture is stirred for 3 days. Then, the solvent is removed in vacuo. The residue is poured into a mixture of ethyl acetate and water. The organic layer is washed with brine and dried. The solvent is removed in vacuo. The residue is purified by silica gel column chromatography (solvent; hexane:ethyl acetate=1:3) to give 6.54 g of methyl. (2S,3R)-3-cyclopropyl-3-hydroxy-2-(p-toluenesulfonyloxy)propionate.

Yield: 79% m.p.: 75°–78° C. MS(m/z): 312($M^+$−2) IR(neat,$cm^{-1}$): 3520,1760

NMR($CDCl_3$,δ): 0.16–0.26(1H,m), 0.36–0.46(2H, m), 0.53–0.65(1H,m), 0.90–1.05(1H,m), 2.11(1H,d,J=7Hz), 2.45(3H,s), 3.26(1H,ddd,J=4,7,10Hz), 3.69(3H,s), 4.93(1H, d,J=4Hz), 7.32–7.38(2H,m), 7.82–7.88(2H,m).

(4) To a solution of 2.97 g of methyl (2S,3R)-3-cyclopropyl-3-hydroxy-2-(p-toluenesulfonyloxy)propionate in 50 ml of acetonitrile are added 10.86 ml of water and 3.96 g of potassium carbonate successively at room temperature. Then, the reaction mixture is stirred at 50° C. for 2 days. The reaction mixture is cooled to room temperature, and insoluble materials are removed by filtration. The filtrate is concentrated under reduced pressure. The residue is purified by silica gel column chromatography (solvent; diethylether) to give methyl (2R,3R)-3-cyclopropyl-2,3-epoxypropionate quantitatively. MS(m/z): 142($M^+$) IR(neat,$cm^{-1}$): 1750

NMR($CDCl_3$, δ): 0.36–0.44(1H,m), 0.52–0.76(3H,m), 0.86–0.98(1H,m), 2.58(1H, dd,J=4,8Hz), 3.56(1H,d,J=4Hz), 3.83(3H, s).

(5) To a solution of 2.89 g of methyl (2R,3R)-3-cyclopropyl-2,3-epoxypropionate in 112.5 ml of methanol-water (8:1) are added 14 ml of methyl formate and 16.60 g of sodium azide. Then, the reaction mixture is stirred at 50° C. overnight. The reaction mixture is cooled to room temperature and evaporated to remove methanol. The residue is dissolved in ethyl acetate. The solution is washed with brine and dried. The solvent is removed in vacuo. The residue is purified by silica gel column chromatography (solvent; hexane:ethyl acetate=4:1) to give 2.61 g of methyl (2R,3S)-3-cyclopropyl-3-azido-2-hydroxypropionate.

Yield: 70% $[\alpha]_D^{23}$–67.19° (c=1,chloroform) FAB-MS(m/z): 186(MH$^+$) IR(neat,cm$^{-1}$): 3480,2100,1740

NMR($CDCl_3$, δ): 0.29–0.39(1H,m), 0.50–0.59(1H,m), 0.63–0.73(1H,m), 0.80–0.90(1H,m), 1.37–1.51(1H,m), 2.83(1H,dd,J=2,10 Hz), 3.06(1H,d,J=7 Hz), 4.29(1H,dd,J=2,7 Hz).

(6) To a solution of 1.82 g of methyl (2R,3S)-3-cyclopropyl-3-azido-2-hydroxypropionate in 60 ml of ethyl acetate are added 600 mg of 10% palladium-carbon and 2.57 g of t-butoxycarboxylic anhydride. The mixture is stirred under the atmospheric pressure of hydrogen at room temperature for one hour. The inorganic materials are removed by filtration, and the filtrate is condensed. The residue is purified by silica gel column chromatography (solvent; hexane:ethyl acetate=2:1) to give 2.78 g of methyl (2R,3S)-3-cyclopropyl-3-tert-butoxycarbonylamino-2-hydroxypropionate.

Yield: 100% m.p.: 93° C. $[\alpha]_D^{23}$ –59.79° (c=1,chloroform) FAB-MS(m/z): 260(MH$^+$) IR(nujol, cm$^{-1}$): 3520,3440,3320,1740,1720,1710,1690

NMR($CDCl_3$, δ): 0.32–0.39(1H,m), 0.41–0.51(1H, m), 0.51–0.62(2H, m), 1.07–1.21(1H,m), 1.41(9H,s), 3.19(1H, d,J=5 Hz), 3.29(1H, dt,J=2,10 Hz), 3.78(3H,s), 4.31(1H,dd, J=2,5 Hz), 4.90(1H,dlike).

(7) To a solution of 2.63 g of methyl (2R,3S)-3-cyclopropyl-3-tert-butoxycarbonylamino-2-hydroxypropionate in 60 ml of benzene are added 1.94 ml of isopropenylmethylether and 0.25 g of p-toluenesulfonic acid pyridinium salt. The mixture is stirred at room temperature for one hour, and then refluxed for 40 minutes. After the mixture is cooled, 1.94 ml of isopropenylmethylether is added to the reaction mixture. The mixture is stirred at room temperature for 10 minutes, refluxed for 40 minutes, and evaporated to remove the solvent. The residue is purified by silica gel column chromatography (solvent; hexane:ethyl acetate=8:1) to give 2.69 g of methyl (4S,5R)-3-tert-butoxycarbonyl-2,2-dimethyl-4-cyclopropyl-5-oxazolidinecarboxylate.

Yield: 89% MS(m/z): 299(M$^+$) IR(neat,cm$^{-1}$): 1760,1720,1700

NMR($CDCl_3$,δ): 0.23–0.33(1H,m), 0.43–0.54(1H,m), 0.61–0.76(2H,m), 1.10–1.22(1H,m), 1.49(9H,s), 1.62(3H,s), 1.64(3H,s), 3.73–3.88(1H,m), 3.77(3H,s), 4.42(1H,d,J=2.0 Hz).

(8) To a solution of 2.66 g of methyl (4S,5R)-3-tert-butoxycarbonyl-2,2-dimethyl-4-cyclopropyl-5-oxazolidinecarboxylate in 60 ml of methanol is added dropwise a solution of 255 mg of lithium hydroxide in 30 ml of water under ice-cooling. The reaction mixture is warmed to room temperature, stirred for one hour and evaporated under reduced pressure to remove methanol. Chloroform is added to the residue. The pH of the mixture is adjusted to about pH 2 with 10% hydrochloric acid under ice-cooling thereto. The chloroform layer is washed with brine, dried, and evaporated under reduced pressure to remove the solvent to give 2.65 g of (4S,5R)-3-tert-butoxycarbonyl-2,2-dimethyl-4-cyclopropyl-5-oxazolidinecarboxylic acid.

Yield: 100% m.p.: 104°–108° C. FAB-MS(m/z): 286(MH$^+$) IR(nujol, cm$^{-1}$): 3080,1720,1690

NMR($CDCl_3$, δ): 0.27–0.38(1H,m), 0.45–0.56(1H,m), 0.62–0.76(2H,m), 1,11–1.24(1H,m), 1.49(9H,s), 1.65(3H,s), 1.66(3H,s), 3.75–3.88(1H,m), 4.45(1H,d,J=2 Hz), 6.60(1H, brs).

(9-1) To a solution of 1.20 g of (4S,5R)-3-tert-butoxycarbonyl-2,2-dimethyl-4-cyclopropyl-5-oxazolidinecarboxylic acid and 2.5 g of 4α-acetoxy-2α-benzoyloxy-5β, 20-epoxy-1β,13α-dihydroxy-7β,10β-bis(2,2,2-trichloroethoxycarbonyloxy)tax-11-en-9-one in 60 ml of toluene are added 922 mg of 1,3-dicyclohexylcarbodiimide and 171 mg of 4-dimethylaminopyridine. The mixture is stirred at 80° C. for 90 minutes. Insoluble materials are removed from the reaction mixture by filtration, and the filtrate is evaporated in vacuo. The residue is purified by silica gel column chromatography (solvent; hexane:ethyl acetate=3:1) to give 3.1 g of 4α-acetoxy-2α-benzoyloxy-13α-[(4S,5R)-3-tert-butoxycarbonyl-2,2-dimethyl-4-cyclopropyloxazolidin-5-ylcarbonyloxy]-5β,20-epoxy-1β-hydroxy-7β,10β-bis(2,2,2-trichloroethoxycarbonyloxy)tax-11-en-9-one.

Yield: 96% FAB-MS(m/z): 1162(MH$^+$) IR(nujol,cm$^{-1}$): 3500,1760,1740,1700

NMR($CDCl_3$,δ): 0.23–0.33(1H,m), 0.45–0.57(1H,m), 0.64–0.80(2H,m), 1.08–1.18(1H,m), 1.20(3H,s), 1.27(3H,s), 1.50(9H,s), 1.58(3H,s), 1.66(6H,s) 1.71(1H,s), 1.85(3H,s), 2.00–2.14(1H,m), 2.08(3H, d,J=1 Hz), 2.24–2.33(2H, m), 2.42(3H,s), 2.64(1H,ddd,J=7,10,14 Hz), 3.90–3.95(1H,m), 3.97(1H,d,J=7 Hz), 4.17(1H,d,J=8 Hz), 4.35(1H,d,J=8 Hz), 4.45(1H,d,J=2 Hz), 4.60(1H,d,J=12 Hz), 4.75(1H,d,J=12 Hz), 4.80(1H,d,J=12 Hz), 4.92(1H,d,J=12 Hz), 4.95–5.01 (1H,m), 5.61(1H,dd,J=711 Hz), 5.70(1H, d,J=7 Hz), 6.18–6.26(1H,m), 6.27(1H,s), 7.46–7.54(2H,m), 7.60–7.67(1H,m), 8.06–8.12(2H,m).

(9-2) To a solution of 85.5 mg of (4S,5R)-3-tert-butoxycarbonyl-2,2-dimethyl-4-cyclopropyl-5-oxazolidinecarboxylic acid in 1 ml of toluene are added under argon atmosphere 44 μl of triethylamine and 38.4 mg of 4-(N,N-dimethylamino)pyridine at 0° C. A solution of 76.7 mg of 2,4,6-trichlorobenzoyl chloride in 1 ml of toluene is added to the mixture. The mixture is stirred at room temperature for 1 hour. Then, to the mixture is added 171.2 mg of 4α-acetoxy-2α-benzoyloxy-5β-20-epoxy-1β,13α-dihydroxy-7β,10β-bis(2,2,2-trichloroethoxycarbonyloxy)tax-11-en-9-one, and the mixture is continued to be stirred at the same temperature for 2 hours. The reaction mixture is diluted with ethyl acetate, washed with 1% hydrochloric acid, saturated aqueous sodium hydrogen carbonate solution, water, and brine in this order, and dried over sodium sulfate. The solvent is removed in vacuo. The residue is purified by silica gel column chromatography (solvent; n-hexane:ethyl acetate=3:2) to give 183 mg of 4α-acetoxy-2α-benzoyloxy-13α-[(4S,5R)-3-tert-butoxycarbonyl-2,2-dimethyl-4-cyclopropyloxazolidin-5-ylcarbonyloxy]-5β-20-epoxy-1β-hydroxy-7β,10β-bis(2,2,2-trichloroethoxycarbonyloxy)tax-11-en-9-one. The physical properties of the product are the same as those of the compound of Example 1(9-1).

(10) A solution of 3.04 g of 4α-acetoxy-2α-benzoyloxy-13α-[(4S,5R)-3-tert-butoxycarbonyl-2,2-dimethyl-4-cyclopropyloxazolidin-5-ylcarbonyloxy]-5β,20-epoxy-1β-hydroxy-7β,10β-bis(2,2,2-trichloroethoxycarbonyloxy)tax-11-en-9-one in 50 ml of formic acid is stirred at room temperature for 2 hours. After formic acid is removed in vacuo, the reaction mixture is crystallized from ethanol-diisopropylether. Crystals are collected by filtration, washed with diisopropylether and then dried to give 2.54 g of 4α-acetoxy-2α-benzoyloxy-13α-[(2R,3S)-3-amino-3-cyclopropyl-2-hydroxypropionyloxy]-5β,20-epoxy-1β-hydroxy-7β,10β-bis(2,2,2-trichloroethoxycarbonyloxy)tax-11-en-9-one formate.

Yield: 91% m.p.: 154°–172° C. (decomposed) FAB-MS(m/z): 1022($MH^+$) IR(nujol,$cm^{-1}$): 3440,1760,1720

NMR($CDCl_3$,δ): 0.28–0.40(1H,m), 0.43–0.57(1H,m), 0.57–0.78(2H,m), 1.10–1.15(1H,m), 1.18(3H,s), 1.23(3H,s), 1.84(3H,s), 2.00–2.12(1H,m), 2.24–2.32(2H,m), 2.39(3H,s), 2.55–2.69(1H,m), 2.69–2.78(1H,m), 3.90(1H,d,J=7 Hz), 4.16(1H,d,J=8 Hz), 4.20–4.62(5H,m), 4.33(1H,d,J=8 Hz), 4.48(1H,d,J=6 Hz), 4.59(1H,d,J=12 Hz), 4.77(2H,slike), 4.87(1H,d,J=12 Hz), 4.94–5.00(1H,m,) 5.53(1H,dd,J=7,11 Hz), 5.69(1H,d,J=7 Hz), 6.20–6.29(1H,m), 6.23(1H,s), 7.45–7.53(2H,m), 7.57–7.66(1H,m), 8.03–8.10(2H,m), 8.32(1H,brs).

(11) To a solution of 600 mg of 4α-acetoxy-2α-benzoyloxy-13α-[(2R,3S)-3-amino-3-cyclopropyl-2-hydroxypropionyloxy]-5β,20-epoxy-1β-hydroxy-7β,10β-bis(2,2,2-trichloroethoxycarbonyloxy)tax-11-en-9-one formate in 15 ml of tetrahydrofuran are added dropwise a solution of 169 mg of potassium bicarbonate and 245 mg of tert-butoxycarboxylic anhydride in 5 ml of tetrahydrofuran. The mixture is stirred for 2.5 hours at room temperature. Inorganic materials are removed by filtration. Ethyl acetate is added to the filtrate. The mixture is washed with a saturated aqueous sodium bicarbonate solution, water and brine and dried. The solvent is removed in vacuo. The residue is purified by silica gel column chromatography (solvent; hexane:ethyl acetate=2:1) to give 471 mg of 4α-acetoxy-2α-benzoyloxy-13α-[(2R,3S)-3-tert-butoxycarbonylamino-3-cyclopropyl-2-hydroxypropionyloxy]-5β,20-epoxy-1β-hydroxy-7β,10β-bis(2,2,2-trichloroethoxycarbonyloxy)tax-11-en-9-one.

Yield: 75%

FAB-MS(m/z): 1122($MH^+$) IR(nujol,$cm^{-1}$): 3440,1760, 1720

NMR($CDCl_3$,δ): 0.24–0.32(1H,m), 0.43–0.52(1H,m), 0.61–0.70(2H, m), 1.18–1.32(1H,m), 1.20(3H,s), 1.27(3H, s), 1.34(9H,s), 1.71(3H,s), 1.86(3H,s), 2.02(3H,d=1Hz), 2.05–2.13(1H,m), 2.30–2.38(2H,m), 2.39(3H,s), 2.64(1H, ddd,J=7,10,14 Hz), 3.31 (1H,dt,J=2,9 Hz), 3.34(1H,d,J=6 Hz), 3.91 (1H,d,J=7 Hz), 4.18(1H,d,J=8 Hz), 4.34(1H, d,J=8 Hz), 4.40(1H,dd,J=2,6 Hz), 4.60(1H,d,J=12 Hz), 4.75(1H, d,J=12 Hz), 4.80(1H,d,J=12 Hz), 4.88–4.93(1H,m), 4.91 (1H,d,J=12 Hz), 4.98(1H,d,J=8 Hz), 5.56(1H,dd,J=7,11 Hz), 5.71(1H,d,J=7 Hz), 6.11–6.20(1H,m), 6.26(1H,s), 7.47–7.54(2H,m), 7.59–7.66(1H,m), 8.08–8.13(2H,m).

(12) To a solution of 181 mg of ((3S)-3-benzyloxycarbonylamino-3-ethoxycarbonylpropionyloxy)acetic acid and 479 mg of 4α-acetoxy-2α-benzoyloxy-13α-[(2R,3S)-3-tert-butoxycarbonylamino-3-cyclopropyl-2-hydroxypropionyloxy]-5β,20-epoxy-1β-hydroxy-7β,10β-bis(2,2,2-trichloroethoxycarbonyloxy)tax-11-en-9-one in 20 ml of tetrahydrofuran are added 106 mg of 1,3-dicyclohexylcarbodiimide and 5.2 mg of 4-dimethylaminopyridine. The mixture is stirred at 60° C. for 2 hours. Insoluble materials are removed by filtration, and the filtrate is evaporated under reduced pressure. The residue is purified by silica gel column chromatography (solvent; chloroform:methanol=60:1), and then silica gel column chromatography (solvent; hexane:ethyl acetate=2:1) to give 496 mg of 4α-acetoxy-2α-benzoyloxy-13α-{(2R,3S)-3-tert-butoxycarbonylamino-2-[(3S)-3-benzyloxycarbonylamino-3-ethoxycarbonylpropionyloxyacetoxy]-3-cyclopropylpropionyloxy}-5β,20-epoxy-1β-hydroxy-7β,10β-bis(2,2,2-trichloroethoxycarbonyloxy)tax-11-en-9-one.

Yield: 80% m.p.: 107°–121° C. (decomposed) FAB-MS(m/z): 1479($MH^+$+Na) IR(nujol,$cm^{-1}$): 3380,1760,1720

NMR($CDCl_3$, δ): 0.20–0.26(1H,m), 0.46–0.51 (1H,m), 0.61–0.67(2H,m), 106–1.08(1H,m), 1.19(3H,s), 1.24(3H,s), 1.25–1.30(3H,m), 1.32(9H,s), 1.69(1H,s), 1.85(3H,s), 2.04(3H,s), 2.05–2.10(1H,m), 2.23–2.35(2H,m), 2.37(3H,s), 2.58–2.67(1H,m), 2.96–3.04(1H,m), 3.13–3.21(1H,m), 3.55–3.62(1H,m), 3.91 (1H,d,J=7 Hz), 4.17(1H,d,J=8 Hz), 4.19–4.28(2H,m), 4.34(1H,d,J=8 Hz), 4.58(1H,d,J=12 Hz), 4.64–4.70(1H,m), 4.73(1H,d,J=16 Hz), 4.74(1H,d,J=6 Hz), 4.74(1H,d,J=12 Hz), 4.78(1H,d,J=12 Hz), 4.85(1H,d,d,J=16 Hz), 4.89(1H,d,J=12 Hz), 4.98(1H,dlike,J=9 Hz), 5.09–5.21 (5H,m), 5.56(1H,dd,J=7,11 Hz), 5.70(1H,d,J=7 Hz), 5.81(1H,dlike,J=8 Hz), 6.12–6.19(1H,m), 6.25(1H,s), 7.29–7.38(5H,m), 7.50(2H,tlike), 7.62(1H,t,J=7 Hz), 8.10(2H,d,J=7 Hz).

(13) To a solution of 262 mg of 4α-acetoxy-13α-{(2R, 3S)-3-tert-butoxycarbonylamino-2-[(3S)-3-benzyloxycarbonylamino-3-ethoxycarbonylpropionyloxyacetoxy]-3-cyclopropylpropionyloxy}-2α-benzoyloxy-5β, 20-epoxy-1β-hydroxy-7β,10β-bis(2,2,2-trichloroethoxycarbonyloxy)tax-11-en-9-one in a mixture of 20 ml of methanol and 4 ml of acetic acid is added 352 mg of zinc powder. The mixture is stirred at 60° C. for 30 minutes. Inorganic materials are removed by filtration, and the filtrate is evaporated under reduced pressure. The residue is extracted with ethyl acetate by adding ethyl acetate and water. The extract is washed with 1% hydrochloric acid, water and a saturated aqueous sodium successively, and the solvent is removed in vacuo. The residue is purified by silica gel column chromatography (solvent; chloroform: methanol=50:1) to give 155 mg of 4α-acetoxy-13α-{(2R,3S)-3-tert-butoxycarbonylamino-2-[(3S)-3-benzyloxycarbonylamino-3-ethoxycarbonylpropionyloxyacetoxy]-3-cyclopropylpropionyloxy}-2α-benzoyloxy-5β,20-epoxy-1β,7β,10β-trihydroxytax-11-en-9-one.

Yield: 78% FAB-MS(m/z): 1107($MH^+$) IR(nujol,$cm^{-1}$): 3400,1750, 1700

NMR($CDCl_3$,δ): 0.20–0.28(1H,m), 0.43–0.52(1H,m), 0.58–0.66(2H,m), 0.97–1.07(1H,s), 1.12(3H,s), 1.20(3H,s), 1.27(3H,t,J=7 Hz), 1.32(9H,s), 1.60–1.73(1H,m), 1.68(1H, s), 1.75(3H,s), 1.79–1.90(1H,m), 1.92(3H,brs), 2.15–2.28(2H,m), 2.31(3H,s), 2.52–2.66(1H,m), 2.99(1H, dd,J=4,17 Hz), 3.19(1H,dd,J=4,17 Hz), 3.55–3.66(1H,m), 3.90(1H,d,J=7 Hz), 4.15–4.28(5H,m), 4.31 (1 H,d,J=8 Hz), 4.64–4.83(3H,m), 4.78(2H,d,J=8 Hz), 4.93–4.99(1H,m), 5.08–5.17(1H,m), 5.14(2H,slike), 5.18–5.27(2H,m), 5.68(1H,d,J=7 Hz), 5.88–5.97(1H,m), 6.11–6.21 (1H,m), 7.30–7.38(5H,m), 7.46–7.53(2H,m), 7.57–7.65(1H,m) 8.07–8.14(2H,m).

(14) To a solution of 243 mg of 4α-acetoxy-13α-{(2R, 3S)-3-tert-butoxycarbonylamino-2-[(3S)-3-benzyloxycarbonylamino-3-ethoxycarbonylpropionyloxyacetoxy]-3-cyclopropyl-propionyloxy}-2α-benzoyloxy-5β, 20-epoxy-1β, 7β,10β-trihydroxytax-11-en-9-one in 35 ml of tetrahydrofuran are added 150 mg of 10 % palladium-carbon and 0.032 mg of methanesulfonic acid. The mixture is stirred under the atmospheric pressure of hydrogen at room temperature for 45 minutes. Inorganic materials are removed by filtration, and the filtrate is removed in vacuo. Diethylether is added to the residue to precipitate crystals. Crystals are collected by filtration, washed with diethylether, and dried to give 174 mg of 4α-acetoxy-2α-benzoyloxy-13α-{(2R,3S)-3-tert-butoxycarbonylamino-2-[(3S)-3-amino-3-ethoxycarbonylpropionyloxyacetoxy]-3-cyclopropylpropionyloxy}5β,20-epoxy-1β,7β,10β-trihydroxytax-11-en-9-one methanesulfonate.

Yield: 74% m.p.: 151° C.(decomposed) FAB-M S(m/z): 973($MH^+$) IR(nujol,$cm^{-1}$): 3400,1740,1700

NMR(DMSO-$d_6$, δ): 0.20–0.30(1H,m), 0.32–0.42(1H,m), 0.48–0.57(2H,m), 1.00–1.06(1H,m), 1.02(3H,s), 1.04(3H,s), 1.24(3H,t,J=7 Hz), 1.35(9H,s), 1.55(3H,s), 1.60–1.75(1H,m), 1.79(3H,s), 2.18–2.29(3H,m), 2.31 (6H,s), 3.04(1H,dd,J=6,18 Hz), 3.11 (1H,dd,J=6,18 Hz), 3.37–3.48(1H,m), 3.75(1H,d,J=7 Hz), 4.02–4.13(4.16–4.28(2H,m), 4.40(1H,t,J=6 Hz), 4.65(1H,s), 4.90(2H,s), 4.92–4.98(2H,m), 5.03(1H,d,J=7 Hz), 5.07(1H, d,J=4 Hz), 5.14(1H,s), 5.47(1H,d,J=7 Hz), 5.90–6.00(1H, m), 7.18(1H,D,J=9 Hz), 7.52–7.60(2H,m), 7.63–7.71 (1H, m), 7.98–8.05(2H,m), 8.38(3H,brs).

Example 2

To a solution of 818 mg of 4 α-acetoxy-2α-benzoyloxy-13α-[(2R,3S)-3-tert-butoxycarbonylamino-3-cyclopropyl-2-hydroxypropionyloxy]-5β,20-epoxy-1β-hydroxy-7β,10β-bis(2,2,2-trichloroethoxycarbonyloxy)tax-11-en-9-one obtained in Example 1(11) in a mixture of 75 ml of methanol and 15 ml of acetic acid is added 1.43 g of zinc powder. The mixture is stirred at 60° C. for 30 minutes. After the reaction mixture is cooled to room temperature, insoluble materials are removed by filtration, and the filtrate is evaporated in vacuo. To the residue is added a mixture of ethyl acetate and water. The organic layer is washed with cold 1% hydrochloric acid, water, saturated sodium bicarbonate and brine and. The solvent is removed in vacuo. The residue is purified by silica gel column chromatography (solvent; chloroform:methanol=30:1) to give 512 mg of crude crystals. The crude crystals are washed with a mixture of diisopropylether-hexane and dried to give 476 mg of 4α-acetoxy-2α-benzoyloxy-13α-[(2R,3S)-3-tert-butoxycarbonylamino-3-cyclopropyl-2-hydroxypropionyloxy]-5β,20-epoxy-1β,7β,10β-trihydroxytax-11-en-9-one.

Yield: 85% m.p.: 173–179° C. $[\alpha]_D^{22}$–55.59° (c=1,chloroform) FAB-MS(m/z): 772 ($MH^+$) IR(nujol,$cm^{-1}$): 3400,1700

NMR($CDCl_3$, δ): 0.23–0.32(1H,m), 0.42–0.52(1H,m), 0.59–0.68(2H,m), 1.13(3H,s), 1.19–1.29(1H,m), 1.23(3H,s), 1.33(9H,s), 1.58–1.67(1H,m), 1.69(1H,s), 1.79–1.91(1H,m), 1.93(3H,d,J=1 Hz), 2.29(2H,d,J=9 Hz), 2.37(3H,s), 2.59(1H,ddd,J=7,10,14 Hz), 3.32(1H,dt,J=2,9 Hz), 3.46(1H, d,J=6 Hz), 3.92(1H,d,J=7 Hz), 4.19(1H,d,J=8 Hz), 4.2–4.3(1H,m), 4.21(1H, d,J=2 Hz), 4.34(1H,d,J=8 Hz), 4.39(1H,dd,J=2,6 Hz), 4.90–5.00(2H,m), 5.22(1H,d,J=2 Hz), 5.69(1H,d,J=7 Hz), 6.12–6.22(1H,m), 7.46–7.54(2H, m), 7.57–7.65(1H,m), 8.07–8.13(2H,m).

Example 3

(1) A solution of 4α-acetoxy-2α-benzoyloxy-13α-[(2R,3S)-3-amino-3-cyclopropyl-2-hydroxypropionyloxy]-5β,20-epoxy-1 β-hydroxy-7β,10β-bis(2,2,2-trichloroethoxycarbonyloxy)tax-11-en-9-one formate obtained in Example 1(10)in ethyl acetate is treated with saturated aqueous sodium bicarbonate solution to give 4α-acetoxy-2α-benzoyloxy-13α-[(2R,3S)-3-amino-3-cyclopropyl-2-hydroxypropionyloxy]-5β, 20-epoxy-1β-hydroxy-7β,10β-bis(2,2,2-trichloroethoxy-carbonyloxy)tax-11-en-9-one. To a solution of 504 mg of the resulting free base in methylene chloride is added 73 mg of t-butylisocyanate at room temperature under argon atmosphere, and the mixture is stirred overnight. Water is added to the reaction mixture, and the mixture is extracted with chloroform. The extract is washed with brine, dried, and evaporated under reduced pressure to remove the solvent. The residue is purified by silica gel column chromatography (solvent; hexane:ethyl acetate=3:1) to give 376 mg of 4α-acetoxy-2α-benzoyloxy-13α-[(2R,3S)-3-tert-butylaminocarbonylamino-3-cyclopropyl-2-hydroxypropionyloxy]-5β,20-epoxy-1β-hydroxy-7β,10β-bis(2,2,2-trichloroethoxycarbonyloxy)tax-11 -en-9-one.

Yield: 68% m.p.: 167°–174° C. FAB-MS(m/z): 1143($M^+$+Na) IR(nujol,$cm^{-1}$): 3400,1760,1720,1660

NMR($CDCl_3$, δ): 0.24–0.31(1H,m), 0.41–0.50(1H,m), 0.54–0.70(2H,m), 1.19–1.28(7H,m), 1.24(9H,s), 1.76(1H,s), 1.86(3H,s), 2.00–2.12(1H,m), 2.03(3H,d,J=1 Hz), 2.25–2.49(2H,m), 2.41 (3H,s), 2.63(1H,ddd,J=7,10,14 Hz), 3.35–3.45(1H,ddlike,J=2,9 Hz), 3.75(1H,d,J=7 Hz), 3.91(1H,d,J=7 Hz), 4.18(1H,d,J=8 Hz), 4.26(1H,br 4.37(1H, d,J=8 Hz), 4.39(1H,dd,J=2,7 Hz), 4.53(1H,d,J=9 Hz), 4.60(1H, d,J=12 Hz), 4.75(1H,d,J=12 Hz), 4.80(1H,d,J=12 Hz), 4.91(1H,d,J=12 Hz), 4.95–5.01 (1H,dlike), 5.56(1H,dd, J=7,11 Hz), 5.72(1H,d,J=7 Hz), 6.10–6.19(1H,m), 6.26(1H, s), 7.47–7.55(2H,m), 7.59–7.67(1H,m), 8.07–8.13(2H,m).

(2) A 355 mg of 4α-acetoxy-2α-benzoyloxy-13α-[(2R,3S)-3-tert-butylaminocarbonylamino-3-cyclopropyl-2-hydroxypropionyloxy]-5β,20-epoxy-1β-hydroxy-7β,10β-bis(2,2,2-trichloroethoxycarbonyloxy)tax-11-en-9-one is treated in the same manner as described in Example 1(12)–(14) to give 158 mg of 4α-acetoxy-13α-{(2R,3S)-3-tert-butylaminocarbonylamino-2-[(3S)-3-amino-3-ethoxycarbonylpropionyloxy)acetoxy]-3-cyclopropylpropionyloxy}-2α-benzoyloxy-5β, 20-epoxy-1β,7β,10β-trihydroxytax-11-en-9-one methanesulfonate.

Yield: 80% m.p.: 165°–169° C. FAB-MS(m/z): 972($MH^+$) IR(nujol, $cm^{-1}$): 3400,1750,1660

NMR(DMSO-$d_6$, δ): 0.08–0.17(1H,m), 0.28–0.37(1H,m), 0.46–0.53(2H,m), 0.97–1.08(1H,m), 1.03(6H,brs), 1.15(9H,brs), 1.23(3H,t,J=7 Hz), 1.54(3H,s), 1.54(3H,s), 1.61–1.72(1H,m), 1.78(3H,s), 2.21–2.36(3H,m), 2.32(3H,s), 2.33(3H,s), 3.04(1H,dd,J=6,18 Hz), 3.12(1H,dd, J=6,18 Hz), 3.74(1H,d,J=7 Hz), 3.75–3.81(1H,m), 4.01–4.13(4.15–4.28(2H,m), 4.40(1H,t,J=6 Hz), 4.62(1H,s), 4.90–5.00(2H,m), 4.90(1H,d,J=16 Hz), 4.96(1H,d,J=16 Hz), 5.05(1H,d,J=7 Hz), 5.10(1H,d,J=3 Hz), 5.14(1H,brs), 5.47(1H,d,J=7 Hz), 5.75(1H,brs), 5.88–5.98(2H,m), 7.53–7.61 (2H,m), 7.63–7.71 (1H,m), 8.01–8.07(2H,m), 8.35(3H,brs).

Example 4

(1-1) To a solution of 500 mg of ethyl (2R,3R)-3-cyclopropyl-2,3-epoxypropionate in 20 ml of tetrahydrofuran is added dropwise 3.52 ml of 1N sodium hydroxide under ice-cooling. The reaction mixture is stirred at room temperature for 2.5 hours. After the reaction mixture is concentrated under reduced pressure, the residue is diluted with 20 ml of water. The reaction mixture is washed with diethylether. The aqueous layer is cooled in an ice-bath. Then, 508 mg of 4-dimethylaminopyridine hydrochloride is added to the mixture. After the resulting mixture is stirred at room temperature for one hour, the reaction mixture is purified by non-ionic absorbing resin HP-20 (Mitsubishi Kasei Kogyo Ltd.) and aqueous eluate is lyophilized to give 503 mg of 4-dimethylaminopyridinium (2R,3R)-3-cyclopropyl-2,3-epoxypropionate. A suspension of 38 mg of 4-dimethylaminopyridinium (2R,3R)-3-cyclopropyl-2,3-epoxypropionate, 45 mg of 4α-acetoxy-2α-benzoyloxy-5β, 20-epoxy-1β,13α-dihydroxy-7β,10β-bis(2,2,2-trichloroethoxycarbonyloxy)tax-11-en-9-one and 31 mg of 1,3-dicyclohexylcarbodiimide in 1 ml of toluene is stirred at 50° C. for one hour. The reaction mixture is cooled to room temperature and diluted with diethylether, and insoluble materials are removed by filtration. The filtrate is washed with brine, dried and evaporated to remove the solvent. The residue is purified by thin layer chromatography (solvent; hexane:ethyl acetate=3:2) to give 45 mg of 4α-acetoxy-2α-benzoyloxy-13α-[(2R,3R)-3-cyclopropyl-2,3-epoxypropionyloxy]-5β,20-epoxy-1β-hydroxy-7β,10β-bis(2,2,2-trichloroethoxycarbonyloxy)tax-11-en-9-one.

Yield: 90% FAB-MS(m/z): 1025($M^+$+Na), 1027([$M^+$+Na]+2), 1029([$M^+$+Na]+4) IR(nujol,$cm^{-1}$): 3480,1760,1720

NMR(300 MHz, $CDCl_3$, δ): 0.42(1H,m), 0.66(2H,m), 0.81(1H,m), 0.95(1H,m), 1.20(3H,S), 1.26(3H,s), 1.70(1H, s,$D_2$ Oexch), 1.86(3H,s), 2.05–2.1(1H,m), 2.09(3H,d,J=1 Hz), 2.25–2.35(2H,m), 2.39(3H,s), 2.63(1H,dd,J=4,9 Hz), 2.64(1H,m), 3.69(1H,d,J=4 Hz), 3.96(1H,d,J=7 Hz), 4.17(1H,d,J=9 Hz), 4.35(1H,d,J=9 Hz), 4.61(1H,d,J=12 Hz), 4.78(1H,d,J=12 Hz), 4.91 (1H,d,J=12 Hz), 4.98(1H,m), 5.59(1H,dd,J=7,11 Hz), 5.69(1H,d,J=7 Hz), 6.27(1H,s), 6.31(1H,m), 7.49(2H,m), 7.63(1H,m), 8.08(2H,m).

(1-2) A 2.04 g of benzyl (2R,3R)-3-cyclopropyl-2,3-epoxypropionate is dissolved in 40 ml of tetrahydrofuran and subjected to catalytic hydrogenation at room temperature under atmospheric pressure using 1 g of 10 % palladium-carbon. After 2 hours, the catalyst is removed by filtration. After 40 ml of toluene is added to the filtrate, the resulting mixture is concentrated under reduced pressure to remove tetrahydrofuran to give a solution of (2R,3R)-3-cyclopropyl-2,3-epoxypropionic acid in toluene. Then, 2.74 g of 4α-acetoxy-2α-benzoyloxy-5β,20-epoxy-1β,13α-dihydroxy-7β,10β-bis(2,2,2-trichloroethoxycarbonyloxy)tax-11-en-9-one, 1.89 g of 1,3-dicyclohexylcarbodiimide and 187 mg of 4-dimethylaminopyridine are added to the resulting solution of (2R,3R)-3-cyclopropyl-2,3-epoxypropionic acid in toluene. The mixture is stirred at 80° C. for one hour. The reaction mixture is cooled to room temperature and treated in the same manner as described in Example 4(1-1). The residue is purified by silica gel frash column chromatography (solvent; ethyl acetate:hexane=1:2) to give 3.02 g of 4α-acetoxy-2α-benzoyloxy-13α-[(2R,3R)-3-cyclopropyl-2,3-epoxypropionyloxy]-5β,20-epoxy-1β-hydroxy-7β,10β-bis(2,2,2-trichloroethoxycarbonyloxy)tax-11-en-9-one. The physical properties of the product are the same as those of the compound of Example 4(1-1).

(2-1) To a solution of 108 mg of 4α-acetoxy-2α-benzoyloxy-13α-[(2R,3R)-3-cyclopropyl-2,3-epoxypropionyloxy]-5β,20-epoxy-1β-hydroxy-7β,10β-bis(2,2,2-trichloroethoxycarbonyloxy)tax-11-en-9-one in 3 ml of methanol-water (8:1) and 0.3 ml of methyl formate is added 211 mg of sodium azide. The reaction mixture is stirred at 50° C. for 15 hours. The reaction mixture is cooled to room temperature, poured into ice-water, and extracted with ethyl acetate. The organic layer is washed with brine, dried and evaporated to remove the solvent. The residue is purified by thin layer chromatography (solvent; chloroform:ethyl acetate=10:1) to give 4α-acetoxy-2α-benzoyloxy-13α-[(2R,3S)-3-azide-3-cyclopropyl-2-hydroxypropionyloxy]-5β,20-epoxy-1β-hydroxy-7β,10β-bis(2,2,2-trichloroethoxycarbonyloxy)tax-11-en-9-one.

Yield: 80% FAB-MS(m/z): 1068($M^+$+Na), 1070([$M^+$+Na]+2), 1072([$M^+$+Na]+4) IR(nujol,$cm^{-1}$): 3500,2110,1760,1720

NMR(300 MHz, $CDCl_3$, δ): 0.35(1H,m), 0.62(1H,m), 0.71(1H,m), 0.91(1H,m), 1.21(3H,s), 1.28(3H,s), 1.47(1H, m), 1.74(1H,s,$D_2$Oexch), 1.87(3H,s), 2.08(1H,m), 2.12(3H, d,J=1 Hz), 2.2–2.3(2H,m), 2.36(3H,s), 2.65(1H,m), 3.05(1H,dd,J=2,10 Hz), 3.11 (1H,d,J=8 Hz,$D_2$Oexch), 3.93(1H,d,J=7 Hz), 4.18(1H,d,J=8 Hz), 4.34(1H,d,J=8 Hz, 4.39(1H,dd,J=2,8 Hz), 4.61(1H,d,J=12 Hz), 4.76(1H,d,J=12 Hz), 4.81(1H,d,J=12 Hz), 4.92(1H,d,J=12 Hz), 4.98(1H,m), 5.57(1H,dd,J=7,11 Hz), 5.70(1H,d,J=7 Hz), 6.22(1H,m), 6.28(1H,s), 7.49(2H,m), 7.63(1H,m), 8.07(2H,m).

(2-2) To a solution of 55 mg of 4α-acetoxy-2α-benzoyloxy-13α-[(2R,3R)-3-cyclopropyl-2,3-epoxypropionyloxy]-5β,20-epoxy-1β-hydroxy-7β,10-bis(2,2,2-trichloroethoxycarbonyloxy)tax-11-en-9-one in 0.5 ml of tetra(n-butyl)tin azide is added catalytic amount of zinc iodide. The reaction mixture is stirred at 50° C. After 19 hours, the reaction mixture is cooled to room temperature and purified by silica gel frash column chromatography (solvent; chloroform-:ethyl acetate=20:1)and thin layer chromatography (solvent; chloroform:ethyl acetate=10:1) to give 51 mg of 4α-acetoxy-2α-benzoyloxy-13-[(2R,3S)-3-azide-3-cyclopropyl-2-hydroxypropionyloxy]-5β,20-epoxy-1β-hydroxy-7β,10β-bis(2,2,2-trichloroethoxycarbonyloxy)tax-11-en-9-one. The physical properties of the product are the same as those of the compound of Example 4(2-1).

(3-1) To a solution of 69 mg of 4α-acetoxy-2α-benzoyloxy-13α-[(2R,3S)-3-azide-3-cyclopropyl-2-hydroxypropionyloxy]-5β,20-epoxy-1β-hydroxy-7β,10β-bis(2,2,2-trichloroethoxycarbonyloxy)tax-11-en-9-one in 3 ml of tetrahydrofuran is added 13 mg of platinum oxide. The reaction mixture is subjected to catalytic hydrogenation at room temperature under atmospheric pressure for 3 hours. After the catalyst is removed by filtration. Then, 0.1 ml of formic acid is added to the filtrate, and the mixture is evaporated to remove the solvent. To the residue is added methanol, and insoluble materials are removed by filtration. Then, the filtrate is evaporated to remove the solvent. The residue is washed to give 46 mg of 4 α-acetoxy-2α-benzoyloxy-13α-[(2R,3S)-3-amino-3-cyclopropyl-2-hydroxypropionyloxy]-5β,20-epoxy-1β-hydroxy-7β,10β-bis(2,2,2-trichloroethoxycarbonyloxy)tax-11-en-9-one formate. The physical properties of the product are the same as those of the compound of Example 1(10).

(3-2) To a solution of 314 mg of 4α-acetoxy-2α-benzoyloxy-13α-[(2R,3S)-3-azide-3-cyclopropyl-2-hydroxypropionyloxy]-5β,20-epoxy-1β-hydroxy-7β,10β-bis(2,2,2-trichloroethoxycarbonyloxy)tax-11-en-9-one in 12 ml of methanol are added 157 mg of 10% palladium-carbon and 305 ml of 1N hydrochloric acid. The mixture is subjected to catalytic hydrogenation at room temperature under atmospheric pressure. After 1.5 hours, the catalyst is removed by filtration. The filtrate is evaporated to remove the solvent. Diisopropylether is added to the residue, and the resulting solid materials are collected by filtration to give 289 mg of 4α-acetoxy-2α-benzoyloxy-13α-[(2R,3S)-3-amino-3-cyclopropyl-2-hydroxypropionyloxy]-5β,20-epoxy-1β-hydroxy-7β,10β-bis(2,2,2-trichloroethoxycarbonyloxy)tax-11-en-9-one hydrochloride.

Yield: 91% FAB-MS(m/z): 1022($MH^+$+2) IR(nujol,$cm^{-1}$): 3410,3140,1760,1740,1730,1710

NMR(DMSO-$d_6$, δ): 0.20–0.27(1H,m), 0.56–0.59(2H,m), 0.64–0.68(1H,m), 1.03(3H,s), 1.07–1.10(1H,m), 1.13(3H,s), 1.72(3H,s), 1.84–1.92(1H,m), 1.99(3H,s), 2.21(1H,dd,J=9,15 Hz), 2.32–2.37(1H,m), 2.37(3H,s), 2.56–2.62(1H,m), 3.81 (1 H,d,J=7 Hz), 4.08–4.15(3H,m), 4.44(1H,brdd,J=6,7 Hz), 4.79(1H,d,J=12 Hz), 4.95(1H, d,J=12 Hz), 4.97(1H,d,J=12 Hz), 5.03(1H,d, J=12 Hz), 5.05(1H,d,J=10 Hz), 5.11 (1H,s), 5.48(1H,dd,J=7,11 Hz), 5.52(1H,d,J=7 Hz), 6.10(1H,brt,J=9 Hz), 6.16(1H, s), 6.94(1H,d,J=5 Hz), 7.57(2H,brt,J=8 Hz), 7.69(1H,brt,J=7 Hz), 7.99(2H,brd,J=7 Hz), 8.28(3H,brs).

(4) 4α-Acetoxy-2α-benzoyloxy-13α-[(2R,3S)-3-amino-3-cyclopropyl-2-hydroxypropionyloxy]-5β,20-epoxy-1β-hydroxy-7β,10β-bis(2,2,2-trichloroethoxycarbonyloxy)tax-11-en-9-one formate is treated in the same manner as described in Example 1 (11) to give 4α-acetoxy-2α-benzoyloxy-13α-[(2R,3S)-3tert-butoxycarbonylamino-3-cyclopropyl-2-hydroxypropionyloxy]-5β,20-epoxy-1β -hydroxy-7β, 10β-bis(2,2,2-trichloroethoxycarbonyloxy)tax-11-en-9-one. The physical properties of the product are the same as those of the compound of Example 1(11).

(5) To a solution of 861 mg of 4α-acetoxy-2α-benzoyloxy-13α-[(2R,3S)-3-tert-butoxycarbonylamino-3-cyclopropyl-2-hydroxypropionyloxy]-5β,20-epoxy-1β-hydroxy-7β,10β-bis(2,2,2-trichloroethoxycarbonyloxy)tax-11-en-9-one in 40 ml of tetrahydrofuran are added 321 mg of benzyloxy acetic acid, a solution of 404 mg of 1,3-dicyclohexylcarbodiimide in 10 ml of tetrahydrofuran and 9 mg of 4-dimethylaminopyridine. The reaction mixture is stirred at room temperature for 1.5 hours and condensed. The residue is dissolved in diethylether, and insoluble materials are removed by filtration. The filtrate is washed, dried and evaporated to remove the solvent. The residue is purified by silica gel frash column chromatography (solvent; hexane:ethyl acetate=3:1) to give 650 mg of 4α-acetoxy-2α-benzoyloxy-13α-[(2R,3S)-3-tert-butoxycarbonylamino-3-cyclopropyl-2-benzyloxyacetoxypropionyloxy]-5β,20-epoxy-1β-hydroxy-7β,10β-bis(2,2,2-trichloroethoxycarbonyloxy)tax-11-en-9-one.

Yield: 67% ESI-MS(m/z): 1292(M+$Na^+$+2), 1290(M+$Na^+$) IR(nujol,$cm^{-1}$): 3444,1760,1725

NMR($CDCl_3$, δ): 0.22–0.26(1H,m), 0.45–0.51(1H,m), 0.60–0.67(2H,m), 1.03–1.11(1H,m), 1.19(3H,s), 1.26(3H,s), 1.33(9H,s), 1.70(1H,s), 1.85(3H,s), 2.2–2.11(1H,m), 2.07(3H,J=1 Hz), 2.29–2.34(2H,m), 2.39(3H,s), 2.65(1H, ddd,J=14,9,7 Hz), 3.59(1H,dt,J=10,2 Hz), 3.93(1H,d,J=7 Hz), 4.17(1H,d,J=9 Hz), 4.25(1H,d,J=17 Hz), 4.31(1H,d,J=17 Hz), 4.35(1H,d,J=1 Hz), 4.60(1H,d,=12 Hz), 4.69(2H,s), 4.75(1H,d,J=12 Hz), 4.79(1H,d,J=12 Hz), 4.86–4.89(1H,m), 4.92(1H,d,J=12 Hz), 4.99(1H,d,J=8 Hz), 5.20(1H,d,J=2.0 Hz), 5.58(1H,dd,J=7,11 Hz), 5.71(1 H,d,J=7 Hz), 6.15–6.21(1H,m), 6.26(1H,s), 7.32–7.40(5H,m), 7.51 (2H, t,J=8 Hz), 7.63(1H,tt,J=1,7 Hz), 8.11(2H,brdd,J=2,9 Hz).

(6) To a solution of 129 mg of 4α-acetoxy-2α-benzoyloxy-13α-[(2R,3S)-3-tert-butoxycarbonylamino-3-cyclopropyl-2-benzyloxyacetoxypropionyloxy]-5β,20-epoxy-1β-hydroxy-7β,10β-bis(2,2,2-trichloroethoxycarbonyloxy)tax-11-en-9-one in 9 ml of tetrahydrofuran-acetic acid (1:2) is added 271 mg of 10 % palladium-carbon. The reaction mixture is subjected to catalytic hydrogenation at room temperature under atmospheric pressure for 2.5 hours. After the catalyst is removed by filtration, the filtrate is evaporated to remove the solvent. The residue is dissolved in ethyl acetate, washed with brine, dried and evaporated to remove the solvent. The residue is purified by silica gel frash column chromatography (solvent; hexane:ethyl acetate=2:1) to give 75 mg of 4α-acetoxy-2α-benzoyloxy-13α-[(2R,3S)-3-tert-butoxycarbonylamino-3-cyclopropyl-2-hydroxyacetoxypropionyloxy]-5β,20-epoxy-1β-hydroxy-7β,10β-bis(2,2,2-trichloroethoxycarbonyloxy)tax-11-en-9-one.

Yield: 63% ESI-MS(m/z): 1202(M+$Na^+$+2), 1200(M+$Na^+$) IR(nujol,$cm^{-1}$): 3445,1756,1725

NMR($CDCl_3$, δ): 0.22–0.29(1H,m), 0.47–0.53(1H,m), 0.63–0.67(2H,m), 1.02–1.12(1H,m), 1.23(3H,s), 1.25(3H,s), 1.34(9H,s), 1.72(1H,s), 1.85(3H,s), 2.02–2.11(1H,m), 2.06(3H,d,J=1 Hz), 2.27–2.36(2H,m), 2.39(3H,s), 2.45(1H, brt,J=6 Hz), 2.64(1H,ddd,J=7,10,14 Hz), 3.59(1H,dt,J=3,10 Hz), 3.92(1H, d,J=7 Hz), 1H,d,J=9 Hz), 4.32(1H,dd,J=3,18 Hz), 4.35(1H,d,J=9 Hz), 4.41 (1H,dd,J=5,18 Hz), 4.60(1H, d,J=12 ), 4.75(1H,d,J=12 Hz), 4.79(1H,d,J=12), 4.91(1H,d, J=10 Hz), 4.92(1H,d,J=12 Hz), 4.99(1H,brd,J =10 Hz), 5.22(1H,d,J=2 Hz), 5.58(1H,dd,J=7,11 Hz), 5.71(1H,d,J=7 Hz), 6.13–6.20(1H,m), 6.26(1H,s), 7.51(2H,t,J=8 Hz), 7.63(1H,tt,J=2,8 Hz), 8.10(2H,brdd,J=1,9 Hz).

(7) To a solution of 56 mg of 4α-acetoxy-2α-benzoyloxy-13α-[(2R,3S)-3-tert-butoxycarbonylamino-3-cyclopropyl-2-hydroxyacetoxypropionyloxy]-5β,20-epoxy-1β-hydroxy-7β,10β-bis(2,2,2-trichloroethoxycarbonyloxy)tax-11-en-9-one in 3 ml of tetrahydrofuran are added 31 mg of (3S)-3-benzyloxycarbonylamino-3-carbamoylpropionic acid, 25 mg of 1,3-dicyclohexylcarbodiimide and about 1 mg of 4-dimethylaminopyridine. The reaction mixture is stirred at room temperature for 4 hours and condensed. The residue is dissolved in ethyl acetate and insoluble materials are removed by filtration. The filtrate is washed, dried and evaporated to remove the solvent. The residue is purified by thin layer chromatography to give 51 mg of 4α-acetoxy-2α-benzoyloxy-13α-{(2R,3S)-3-tert-butoxycarbonylamino-2-[(3S)-3-benzyloxycarbonylamino-3-carbamoylpropionyloxyacetoxy]-3-cyclopropylpropionyloxy}-5β,20-epoxy-1β-hydroxy-7β,10β-bis(2,2,2-trichloroethoxycarbonyloxy)tax-11-en-9-one.

Yield: 76%

ESI-MS(m/z, ammonium acetate): 1445(M+$NH_4^+$+2) IR(nujol,$cm^{-1}$): 3363,1757,1723

NMR($CDCl_3$, δ): 0.17–0.23(1H,m), 0.49–0.53(1H,m), 0.62–0.69(2H,m), 1.10–1.18(1H,m), 1.18(3H,s), 1.23(3H,s), 1.33(9H,s), 1.72(1H,s), 1.84(3H,s), 2.03(3H,s), 2.03–2.06(1H,m), 2.29–2.32(2H,m), 2.37(3H,s), 2.62(1H, ddd,J=7,10,14 Hz), 2.72(1H,dd,J=5,17 Hz), 3.31(1H,dd,J=4,17 Hz), 3.53(1H,dt,J=3,9 Hz), 3.90(1H,d,J=7 Hz), 4.16(1H,d,J=8 Hz), 4.34(1H,d,J=7 Hz), 4.59(1H,d,J=12 Hz), 4.68(1H,d,J=16 Hz), 4.69–4.73(1H,m), 4.75(1H,d,J=12 Hz), 4.78(1H,d,J=12 Hz), 4.90(1H,d,J=12 Hz), 4.92(1H,d,J=16 Hz), 4.97(1H,brd,J=9 Hz), 5.13(1H,br), 5.14(1H,d,J =12 Hz), 5.16(1H,d,J=12 Hz), 5.55(1H,dd,J=10,7 Hz), 5.70(1H, d,J=10 Hz), 6.02(1H,brs), 6.11–6.21(2H,m), 6.24(1H,s), 6.54(1H,brs), 6.60–6.63(1H,m), 7.35–7.38(5H,m), 7.50(2H, t,J=8 Hz), 7.63(1H,tt,J=7,2 Hz), 8.10(2H,brd,J=7 Hz).

(8) 4α-Acetoxy-2α-benzoyloxy-13α-{(2R,3S)-3-tert-butoxycarbonylamino-2-[(3S)-3-benzyloxycarbonylamino-3-carbamoylpropionyloxyacetoxy]-3-cyclopropylpropionyloxy)tax-}-5β,20-epoxy-1β-hydroxy-7β,10β-bis(2,2,2-trichloroethoxycarbonyloxy)tax-11-en-9-one is treated in the same manner as described in Example 1(13) or Example 2 to give 4α-acetoxy-2α-benzoyloxy-13α-{(2R,3S)-3-tert-butoxycarbonylamino-2-[(3S)-3-benzyloxycarbonylamino-3-carbamoylpropionyloxyacetoxy]-3-cyclopropylpropionyloxy}-5β,20-epoxy-1β,7β,10 62 -trihydroxytax-11-en-9-one.

FAB-MS(m/z): 1078(M+$H^+$) IR(nujol,$cm^{-1}$): 3400,1700

NMR($CDCl_3$, δ): 0.12–0.24(1H,m), 0.45–0.57(1H,m), 0.59–0.72(2H,m), 1.05–1.21(1H,m), 1.13(3H,s), 1.16(3H,s), 1.33(9H,s), 1.62–1.98(1H,m), 1.67(1H,s), 1.71(3H,s), 1.89(3H,s), 2.14–2.38(2H,m), 2.37(3H,s), 2.47–2.62(1H,m), 2.66–2.76(1H,m), 3.38–3.40(1H,m), 3.45–3.59(1H,m), 3.89(1H, d,J=7 Hz), 4.10–4.28(3H,m), 4.32(1H,d,J=9 Hz), 4.66–4.69(2H,m,), 4.86–4.98(1H,m), 4.95(1H,d,J=9 Hz), 5.10(1H,brs), 5.15(2H,brs), 5.24(1H,brs), 5.68(1H,d,J=7 Hz), 6.03–6.28(3H,m), 6.72–6.86(1H,m), 7.31–7.41(5H,m), 7.47–7.55(2H,m), 7.57–7.66(1H,m), 8.11 (2H,d,J=8 Hz).

(9) 4α-Acetoxy-2α-benzoyloxy-13α-{(2R,3S)-3-tert-butoxycarbonylamino-2-[(35)-3-benzyloxycarbonylamino-3- carbamoylpropionyloxyacetoxy]-3-cyclopropylpropionyloxy}-5β,20-epoxy-1β,7β,10β-trihydroxytax-11-en-9-one is treated in the same manner as described in Example 1(14) to give 4α-acetoxy-2α-benzoyloxy-13α-{(2R,3S)-3-tert-butoxycarbonylamino-2-[(3S)-3-amino-3-carbamoylproprionyloxyactoxy]-3-cyclopropylpropionyloxy}-5β,20-epoxy-1β,7β,10β-trihydroxytax-11-en-9-one methanesulfonate. FAB-MS(m/z): 944(M+H$^+$) IR(nujol,cm$^{-1}$): 3400,1740,1700

NMR(DMSO-$d_6$, δ): 0.09–0.19(1H,m), 0.31–0.41(1H,m), 0.47–0.59(2H,m), 0.95–1.10(1H,m), 1.02(3H,s), 1.03(3H,s), 1.35(9H,s), 1.54(3H,s), 1.62–1.72(1H,m), 1.79(3H,s), 2.17– 2.34(3H,m), 2.30(3H, s), 2.32(3H,s), 2.95(1H,dd,J=8,17 Hz), 3.08(1H,ddlike), 3.34–3.47(1H,m), 3.74(1H, d,J=7 Hz), 4.02–4.14(4H,m), 4.67(1H,s), 4.89(2H,s), 4.95(1H,d,J=11 Hz), 4.98(1H,d,=2 Hz), 5.05(1.H,d,J=7 Hz), 5.07(1H,d,J=4 Hz), 5.14(1H,d,J=2 Hz), 5.47(1H,d,J=7 Hz), 5.95(1H,t,J=9 Hz), 7.21 (1H,d,J=9 Hz), 7.56(2H,t,J=8 Hz), 7.62–7.72(2H,m), 7.87(1H,brs), 8.02(2H,d,J=7 Hz), 8.09(3H,brs).

Example 5

(1) To a solution of 202 mg of [(3S)-3-benzyloxycarbonylamino-3-carbamoylpropionyloxy]acetic acid in 4 ml of tetrahydrofuran are added successively 90 ml of triethylamine and 75 ml of isopropyloxycarbonylchloride under argon atmosphere at −10° C. The reaction mixture is stirred for 15 minutes. To the mixture is added slowly a solution of 4α-acetoxy-2α-benzoyloxy-13α-[(2R,3S)-3-tert-butoxycarbonylamino-3-cyclopropyl-2-hydroxypropionyloxy]-5β,20-epoxy-1β,7β,10β-trihydroxytax-11-en-9-one obtained in Example 2 in 2 ml of tetrahydrofuran. The reaction mixture is stirred at −10°–0° C. for 7 hours. To the mixture is added saturated aqueous solution of sodium hydrogen carbonate, and the mixture is extracted with ethyl acetate. The extract is washed, dried and evaporated to remove the solvent. The residue is purified by silica gel column chromatography (solvent; hexane:ethyl acetate:ethanol=15:15:1) to give 73 mg of 4α-acetoxy-2α-benzoyloxy-13α-{(2R,3S)-3-tert-butoxycarbonylamino- 2-[(3S )-3-benzyloxycarbonylamino-3carbamoylpropionyloxyacetoxy]-3-cyclopropylpropionyloxy}-5β,20-epoxy-1β,7β,10β-trihydroxytax-11-en-9-one. The physical properties of the product are the same as those of the compound of Example 4(8).

(2) 4α-Acetoxy-2α-benzoyloxy-13α-{(2R,3S)-3-tert-butoxycarbonylamino-3-[(3S)-3-benzyloxycarbonylamino-3-carbamoylpropionyloxyacetoxy]-3-cyclopropylpropionyloxy}-5β,20epoxy-1β,7β,10β,10β-trihydroxytax-11-en-9-one is treated in the same manner as described in Example 1(14) to give 4α-acetoxy-2α-benzoyloxy-13α-{(2R,3S)-3-tert-butoxycarbonylamino-2-[(3S)-3-amino-3-carbamoylpropionyloxyacetoxy]-3-cyclopropylpropionyloxy}-5β,20-epoxy-1β,7β,10β,10β-trihydroxytax-11-en-9-one methanesulfonate. The physical properties of the product are the same as those of the compound of Example 4(9).

Example 6

(1) A solution of 2.07 g of ethyl (2R,3S)-3-cyclopropyl-3-tert-butoxycarbonylamino-2-hydroxypropionate and 213 mg of pyridinium p-toluenesulfonate in 125 ml of toluene is refluxed under heating. To the mixture is added dropwise a solution of 2.76 g of p-anisaldehydedimethylacetal in 25 ml of toluene for 20 minutes. The reaction mixture is evaporated to remove the generated methanol. The mixture is stirred under heating for 1.5 hours and cooled. After the reaction mixture is condensed under reduced pressure, ethyl acetate and water are added to the residue. The ethyl acetate layer is obtained by separation. The aqueous layer is extracted with ethyl acetate. The extract is washed with water and brine, dried and condensed under reduced pressure. The residue is purified by silica gel column chromatography (solvent; toluene:ethyl acetate=40:l) to give 1.572 g of ethyl (4S,5R)-3-tert-butoxycarbonyl-2-(4-methoxyphenyl)-4-cyclopropyl-5-oxazolidinecarboxylate (diastereomeric mixture).

Yield: 53% The physical properties of the main isomer are only shown. ESI-MS(m/z): 392 (M$^+$H) IR(neat,cm$^{-1}$): 1750, 1703

NMR($CDCl_3$, δ): 0.34–0.42(1H,m), 0.51–0.73(3H,m), 1.10–1.22(1H,m), 1.30(3H,t,J=7 Hz), 1.58(9H,s), 3.63(1H, dd,J=2,9 Hz), 3.82(3H,s), 4.24(1H,q,J=7 Hz), 4.25(1H,q,J=7 Hz), 4.60(1H,d,J=2 Hz), 6.32(1H,s), 6.90(2H,dt,J=2,9Hz).

(2) To a solution of 881 mg of ethyl (4S,5R)-3-tert-butoxycarbonyl-2-(4-methoxyphenyl)-4-cyclopropyl-5-oxazolidinecarboxylate (diastereomeric mixture) in 16 ml of methanol is added dropwise a solution of 64.7 mg of lithium hydroxide in 8 ml of water under cooling, and the mixture is stirred at room temperature for 1 hour. After the reaction mixture is evaporated under reduced pressure to remove methanol, the residue is dissolved in chloroform. The pH of the solution is adjusted to pH 2 with 10% hydrochloric acid. After extracted with chloroform, the extract is washed with brine twice, dried and evaporated to remove the solvent to give 792 mg of (4S,5R)-3-tert-butoxycarbonyl-2-(4-methoxyphenyl)-4-cyclopropyl-5-oxazolidinecarboxylic acid.

Yield: 97%

The physical properties of the main isomer are only shown. ESI-MS(m/z): 386(M+Na)

IR(neat,cm$^{-1}$): 3200,1754,1702,1669

NMR($CDCl_3$, δ): 0.37–0.46(1H,m), 0.51–0.76(3H,m), 1.09–1.21(1H,m), 1.38(9H,s), 3.71(1H,dd,J=2,9 Hz), 3.82(3H,s), 4.40(1H,broads), 4.64(1H,d,J=2 Hz), 6.90(2H, dt,J=2,9 Hz), 7.44(2H,dt,J=2,9 Hz).

(3) To a solution of 722 mg of (4S,5R)-3-tert-butoxycarbonyl-2-(4-methoxyphenyl)-4-cyclopropyl-5-oxazolidinecarboxylic acid in 23 ml of toluene are added 495 mg of dicyclohexylcarbodiimide, 93 mg of 4-(N,N-dimethylamino)pyridine and 1,345 g of 4α-acetoxy-2α-benzoyloxy-5β, 20epoxy-1β,13α-dihydroxy-7β,10βbis(2,2,2-trichloroethoxycarbonyloxy)tax-11-en-9-one at room temperature. The mixture is stirred at 80° C. for 2 hours. Insoluble materials are removed by filtration. The filtrate is condensed under reduced pressure. The residue is purified by silica gel column chromatography (solvent; hexane:ethyl acetate=3:1) to give 1.713 g (92% yield) of 4α-acetoxy-2α-benzoyloxy-13α-[(4S,5R)-3-tert-butoxycarbonyl-(2S)-(4-methoxyphenyl)-4-cyclopropyloxazolidin-5-ylcarbonyloxy]-5β,20-epoxy-1β-hydroxy-7β, 10β-bis(2,2,2-trichloroethoxycarbonyloxy)tax-11-en-9-one and 4α-acetoxy-2α-benzoyloxy-13α-[(4S,5R)-3-tert-butoxycarbonyl-(2R)-(4-methoxyphenyl)-4-cyclopropyloxazolidin-5-ylcarbonyloxy]-5β,20epoxy-1β-hydroxy-7β,10β-bis(2,2,2-trichloroethoxycarbonyloxy)tax-11-en-9-one.

m.p.: 158.8°–165.1° C. ESI-MS(m/z): 1258(M+$NH_4$) IR(nujol,cm$^{-1}$): 3488,1761,1729,1704

NMR($CDCl_3$, δ): 0.38–0.46(1H,m), 0.54–0.90(4H,m), 1.21(3H,s), 1.29(3H,s), 1.37(9H,s), 1.72(1H,s), 1.87(3H,s), 2.03–2.13(1H,m), 2.09(3H,d,J=1 Hz), 2.24–2.38(2H,m), 2.33(3H,s), 2.63–2.72(1H,m), 3.78(1H,dd,J=2,9 Hz), 3.85(3H,s), 3.96(1H,d,J=7 Hz), 4.18(1H,d,J=9 Hz), 4.34(1H,d,J=9 Hz), 4.61 (1H,d,J=12 Hz), 4.73(1H,d,j=2 Hz), 4.78(2H,s), 4.91(1H,d,J=12 Hz), 4.97–5.02(1H,m), 5.61(1H,dd,J=7,11 Hz), 5.71(1H, d,J=7 Hz), 6.25–6.32(1H, m), 6.28(1H,s), 6.37(1H,s), 6.95(2H, dt,J=2,9 Hz), 7.48(2H, m), 7.62(1H,tt,J=1,7 Hz), 8.07(2H,dd,J=1,7 Hz).

m.p.: 176.1°–184.3° C. ESI-MS(m/z): 1258(M+$NH_4$) IR(nujol,$cm^{-1}$): 3325,1761,1728,1708

NMR($CDCl_3$, δ): 0.28–0.37(1H,m), 0.51–0.60(1H,m), 0.76–0.92(3H,m), 1.16(3H,s), 1.23(3H,s), 1.24(9H,s), 1.52(3H,s), 1.67(1H,s), 1.82(3H,s), 2.11–2.23(1H,m), 2.27–2.36(2H,m), 2.28(3H,s), 2.55–2.64(1H,m), 3.79(3H,s), 3.84(1H,dd,J=3,11 Hz), 4.11(1H,d,J=8 Hz), 4.13(1H,d,J=7 Hz), 4.32(1H,d,J=8 Hz), 4.50(1H,d,J=3 Hz), 4.59(1H,d,J=12 Hz), 4.75(1H,d,J=12 Hz), 4.80(1H,d,J=12 Hz), 4.89(1H,d, J=12 Hz), 4.91–4.96(1H,m), 5.10(1H,dd,J=7,11 Hz), 5.66(1H,d,J=7 Hz), 5.97(1H,m), 6.10(1H,s), 1H,s), 6.12(1H, s), 6.87(2H,dt,J=2,9 Hz), 7.26(2H,dt,J=2,9 Hz), 7.49(2H,m), 7.63(1H,tt,J=1,7 Hz), 8.06(2H,dt,J=1,7 Hz).

(4) To a solution of 52.9 mg of 4α-acetoxy-2α-benzoyloxy-13α-[(4S,5R)-3-tert-butoxycarbonyl-2-(4-methoxyphenyl)-4-cyclopropyloxazolidin-5-ylcarbonyloxy]-5β,20-epoxy-1β-hydroxy-7β,10β-bis(2,2,2-trichloroethoxycarbonyloxy)tax-11-en-9-one in 2.1 ml of methanol is added 8.6 mg of p-toluenesulfonic acid monohydrate at room temperature. The mixture is stirred at room temperature for 23 hours. After the reaction mixture is evaporated under reduced pressure to remove methanol, ethyl acetate, and saturated aqueous solution of sodium hydrogen carbonate is added to the residue. The mixture is stirred. The resulting ethyl acetate layer is washed with water and brine, dried, condensed under reduced pressure and purified by preparative thin layer chromatography (solvent; hexane:ethyl acetate=2:1) to give 30.7 mg of 4α--acetoxy-2α-benzoyloxy-13α-[(2R,3S)-3-tert-butoxycarbonylamino-3-cyclopropyl-2-hydroxypropionyloxy]-5β,20epoxy-1β-hydroxy-7β,10β-bis(2,2,2-trichloroethoxycarbonyloxy)tax-11-en-9-one. The physical properties of the product are the same as those of the compound of Example 1(11).

Yield: 64%

(5) 4α-Acetoxy-2α-benzoyloxy-13α-[(2R,3S)-3-tert-butoxycarbonylamino-3-cyclopropyl-2-hydroxypropionyloxy]-5β,20-epoxy-1β-hydroxy-7β,10β-bis(2,2,2-trichloroethoxycarbonyloxy)tax-11-en-9-one and [(3S)-3-benzyloxycarbonylamino-3-ethoxycarbonylpropionyloxy] acetic acid are treated in the same manner as described in Example 1(12)–(14) to give 4α-acetoxy-2α-benzoyloxy-13α-{(2R,3S)-3-tert-butoxycarbonylamino-2-[(3S)-3-amino-3-ethoxycarbonylpropionyloxyacetoxy]-3-cyclopropylpropionyloxy}-5β,20epoxy-1β,7β,10β-trihydroxytax-11-en-9-one methanesulfonate. The physical properties of the product are the same as those of the compound of Example 1(14).

Example 7

(1)Ethyl (4S,5R)-3-tert-butoxycarbonyl-2-(4-methoxyphenyl)-4-cyclopropyl-5-oxazolidinecarboxylate (diastereomeric mixture) obtained in Example 6(1) is purified by column chromatography to give ethyl (4S,5R)-3-tert-butoxycarbonyl-2-(4-methoxyphenyl)-4-cyclopropyl-5-oxazolidinecarboxylate. A 87 mg of lithium hydroxide is added under ice-cooling to a solution of 1.03 g of ethyl (4S,5R)-3-tert-butoxycarbonyl-2-(4-methoxyphenyl)-4-cyclopropyl-5-oxazolidinecarboxylate in a mixture of 20 ml of methanol and 10 ml of water. The mixture is stirred at room temperature for 30 minutes. The reaction mixture is evaporated under reduced pressure to remove methanol. The pH of the solution of the residue in ethyl acetate is adjusted to pH 2 with 1N hydrochloric acid under ice-cooling. After the mixture is extracted with ethyl acetate, the extract is washed with brine, dried and evaporated to remove the solvent to give 1.20 g of (4S,5R)-3-tert-butoxycarbonyl-2-(4-methoxyphenyl)-4-cyclopropyl-5-oxazolidinecarboxylic acid quantitatively. ESI-MS(m/z): 386($M^+$+Na) IR(neat,$cm^{-1}$): 3080, 1755,1702

NMR($CDCl_3$, δ): 0.37–0.46(1H,m), 0.52–0.77(3H,m), 1.11–1.23(1H,m), 1.38(9H,s), 3.71(1H,brd), 3.82(3H,s), 4.65(1H,d,J=2 Hz), 6.34(1H,s), 6.88–6.93(2H,m), 7.42–7.47(2H,m).

(2) To a solution of 980 mg of (4S,5R)-3-tert-butoxycarbonyl-2-(4-methoxyphenyl)-4-cyclopropyl-5-oxazolidinecarboxylic acid and 1.15 g of 4α-acetoxy-2α-benzoyloxy-5β,20epoxy-1β,13α-dihydroxy-7β-triethylsilyloxy-10 β-(2,2,2-trichloroethoxycarbonyloxy)tax-11-en-9-one in 60 ml of toluene are added 594 mg of dicyclohexylcarbodiimide and 110 mg of dimethylaminopyridine. The mixture is stirred at 60° C. for 1 hour. Insoluble materials are removed by filtration. The filtrate is evaporated under reduced pressure to remove the solvent. To the residue is added ethyl acetate and 1% hydrochloric acid, and the mixture is extracted with ethyl acetate twice. The extract is washed with saturated aqueous solution of sodium hydrogen carbonate and brine, dried and evaporated to remove the solvent. The residue is purified by silica gel column chromatography (solvent; hexane:ethyl acetate=2:1) to give 1.68 g of 4α-acetoxy-2α-benzoyloxy-13α-[(4S,5R)-3-tert-butoxycarbonyl-3-tert-2-(4-methoxyphenyl)-4-cyclopropyloxazolidin-5-ylcarbonyloxy]-5β20-epoxy-1β-hydroxy-7β-triethylsilyloxy-10β-(2,2,2-trichloroethoxycarbonyloxy)tax-11-en-9-one quantitatively.

m.p.: >130° C. (slowly decomposed) ESI-MS(m/z): 1196($M^+$+$NH_4$) IR(nujol,$cm^{-1}$): 1730,1460,1380,1245

NMR($CDCl_3$, δ): 0.36–0.46(1H,m), 0.53–0.86(3H,m), 0.60(6H,brq), 0.94(9H,t,J=7 Hz), 1.20–1.30(1H,m), 1.24(3H,s), 1.26(3H,s), 1.36(9H,s), 1.72(4H,s), 1.86–1.97(1H,m), 2.11(3H,d,J=1 Hz), 2.23–2.36(2H,m), 2.31(3H,s), 2.51–2.64(1H,m), 376(1H,dd,J=2,9 Hz), 3.82(1H,d,J=7 Hz), 3.84(3H,s), 4.17(1H,d,J=8 Hz), 4.31(1H,d,J=8 Hz), 4.50 (1H, dd,J=7,10 Hz), 4.73(1H,d,J=2 Hz), 4.80(2H,s), 4.96(1H,d,J=8 Hz), 5.70(1H,d,J=7 Hz), 6.26(1H,brt), 6.30(1H,s), 6.38(1H,s), 6.92–6.98(2H,m), 7.44–7.56(4H,m), 7.57–7.64(1H, m), 8.03–8.10(2H,m).

(3) To a solution of 40 mg of 4α-acetoxy-2α-benzoyloxy-13α-[(4S,5R)-3-tert-butoxycarbonyl-2-(4-methoxyphenyl)-4-cyclopropyloxazolidin-5-ylcarbonyloxy]-5β, 20-epoxy-1β-hydroxy-7β-triethylsilyloxy-10β-(2,2,2-trichloroethoxycarbonyloxy)tax-11-en-9-one in 1 ml of methanol is added 14 mg of p-toluenesulfonic acid monohydrate at room temperature. The mixture is stirred at room temperature for 2 hours. Then, 14 mg of p-toluenesulfonic acid monohydrate is added thereto. The mixture is stirred at room temperature for 4 hours. After the reaction mixture is condensed, the residue is extracted with ethyl acetate by adding ethyl acetate and saturated aqueous solution of sodium hydrogen carbonate thereto. The extract is washed with brine, dried and evaporated to remove the solvent. The residue is purified by thin layer chromatography (solvent; hexane:ethyl acetate=3:2)to give 22 mg of 4α-acetoxy-2α-benzoyloxy-13α-[(2R,3S)-3-tert-butoxycarbonylamino-3-cyclopropyl-2-hydroxypropionyloxy]-5β,20epoxy-1β,7β-dihydroxy-10β-(2,2,2trichloroethoxycarbonyloxy)tax-11-en-9-one.

Yield: 69% m.p.: >155° C .(slowly decomposed) ESI-MS(m/z): 965($M^+$+$NH_4$),963,948($M^+$+H) IR(neat,$cm^{-1}$): 3520,1720, 1250

NMR($CDCl_3$, δ): 0.22–0.31(1H,m), 0.44–0.53(1H,m), 0.60–0.69(2H,m), 1.20–1.28(1H,m), 1.18(3H,s), 1.28(3H,s), 1.32(9H,s), 1.70(4H,s), 1.83–1.95(1H,m), 1.95(3H,d,J=l Hz), 2.23(1H,d,J=5 Hz), 2.30–2.35(2H,m), 2.37(3H,s), 2.50–2.64(1H,m),3.25–3.33(1H,m), 3.33(1H,d,J=6 Hz), 3.77(1H,d,J=7 Hz), 4.18(1H,d,J=8 Hz), 4.33(1H,d,J=9 Hz), 4.35–4.41(2H,m), 4.77(1H,d,J=12 Hz), 4.88(1H,brd), 4.89(1H,d,J=12 Hz), 4.97(1H,brd), 5.70(1H,d,J=7 Hz), 6.17(1H,s), 6.18(1H,brt), 7.47–7.54(2H,m), 7.59–7.65(1H, m), 8.08–8.13(2H,m).

(4) To a solution of 20 mg of 4α-acetoxy-2α-benzoyloxy-13α-[(2R,3S)-3-tert-butoxycarbonylamino-3-cyclopropyl-2-hydroxypropionyloxy]-5β,20epoxy-1β,7β-dihydroxy-10β-(2,2,2-trichloroethoxycarbonyloxy)tax-11-en-9-one and 7.5 mg of [(3S)-3-benzyloxycarbonylamino-3-carbamoylpropionyloxy]acetic acid in 1.5 ml of dichloromethane are added 5.0 mg of dicyclohexylcarbodiimide and 1.3 mg of dimethylaminopyridine under ice-cooling. The mixture is stirred under ice-cooling for 20 minutes and at room temperature for 4 hours. Insoluble materials are removed by filtration. After the filtrate is condensed under reduced pressure, the residue is extracted with ethyl acetate by adding ethyl acetate and 1% aqueous hydrochloric acid thereto. The extract is washed with saturated aqueous solution of sodium hydrogen carbonate and brine, dried and evaporated to remove the solvent. The residue is purified by thin layer chromatography (solvent; hexane:ethyl acetate= 1:4) to give 13 mg of 4α-acetoxy-2α-benzoyloxy-13α{(2R, 3S)-3-tert-butoxycarbonylamino-2-[(3S)-3-benzyloxycarbonylamino-3-carbamoylpropionyloxyacetoxy]-3-cyclopropylpropionyloxy}-5 β,20-epoxy-1β,7β-dihydroxy-10β-(2,2,2-trichloroethoxycarbonyloxy)tax-11-en-9-one.

Yield: 49% m.p.:>140° C. (slowly decomposed) ESI-MS(m/z): 1269($M^+$+$NH_4$) IR(neat, $cm^{-1}$) : 3360, 1700–1750, 1505

NMR($CDCl_3$, δ): 0.15–0.23(1H,m), 0.47–0.56(1H,m), 0.60–0.70(2H,m), 1.15–1.20(1H,m), 1.16(3H,s), 1.24(3H,s), 1.30(9H,s), 1.69(4H,s), 1.83–1.99(1H,m), 1.96(3H,brs), 2.25–2.35(3H,m), 2.37(3H,s), 2.51–2.63(1H,m), 2.70(1H, dd,J=4,17 Hz), 3.55(1H,brt), 3.77(1H,d,J=7 Hz), 4.17(1H, d,J=8 Hz), 4.32(1H,d,J=9 Hz), 4.33–4.43(1H,m), 4.66–4.74(1H,m), 4.67(1H,d,J=16 Hz), 4.76(1H,d,J=12 Hz), 4.89(1H,d,J=12 Hz), 4.93(1H,d,J=16 Hz), 4.98(1H,brd), 5.10(1H,d,J=3 Hz), 5.15(2H,s), 5.69(1H,d,J=7 Hz), 6.00(1H,br), 6.13–6.21(2H,m), 6.17(1H,s), 6.50(1H, br), 6.74(1H,brd), 7.33–7.39(5H,m), 7.47–7.53(2H,m), 7.58–7.65(1H,m), 8.09–8.14(2H,m).

(5) To a solution of 35 mg of 4α-acetoxy-2α-benzoyloxy-13α-{(2R,3S)-3-tert-butoxycarbonylamino-2-[(3S)-3-benzyloxycarbonylamino-3-carbamoylpropionyloxyacetoxy]-3-cyclopropylpropionyloxy}-5β,20epoxy-1β,7β-dihydroxy-10β-(2,2,2-trichloroethoxycarbonyloxy)tax-11-en-9-one in 2.0 ml of methanol are added 55 mg of zinc and 0.4 ml of acetic acid at room temperature. The mixture is stirred at 40° C. for 2 hours. The solid materials are removed by filtration. After the filtrate is condensed under reduced pressure, the residue is extracted with ethyl acetate by adding ethyl acetate and 1% hydrochloric acid to the residue under ice-cooling. The extract is washed with the saturated aqueous solution of sodium hydrogen carbonate and brine, dried and evaporated to remove the solvent. The residue is purified by thin layer chromatography (solvent; chloroform-:methanol=10:1) to give 24 mg of 4α-acetoxy-2α-benzoyloxy-13α-{(2R,3S)-3-tert-butoxycarbonylamino-2-[(3S)-3-benzyloxycarbonylamino-3-carbamoylpropionyloxyacetoxy]-3-cyclopropylpropionyloxy}-5β,20epoxy-1β,7β,10β-trihydroxytax-11-en-9-one. The physical properties of the product are the same as those of the compound of Example 4(8).

Yield: 80%

(6)4α-acetoxy-2α-benzoyloxy-13α-{(2R,3S)-3-tert-butoxycarbonylamino-2-[(3S)-3-benzyloxycarbonylamino-3-carbamoylpropionyloxyacetoxy]-3-cyclopropylpropionyloxy}-5β,20epoxy-1β,7β,10β-trihydroxytax-11-en-9-one is treated in the same manner as described in Example 1(14) to give 4α-acetoxy-2α-benzoyloxy-13α-{(2R,3S)-3-tert-butoxycarbonylamino-2-[(3S)-3-amino-3-carbamoylpropionyloxyacetoxy]-3-cyclopropylpropionyloxy}-5β,20-epoxy-1β,7β,10β-trihydroxytax-11-en-9-one methanesulfonate. The physical properties of the product are the same as those of the compound of Example 4(9).

Example 8-12

The corresponding starting compounds are treated in the same manner as described in Example 1 or 4–7 to give the compounds shown in Tables 8–11.

TABLE 8

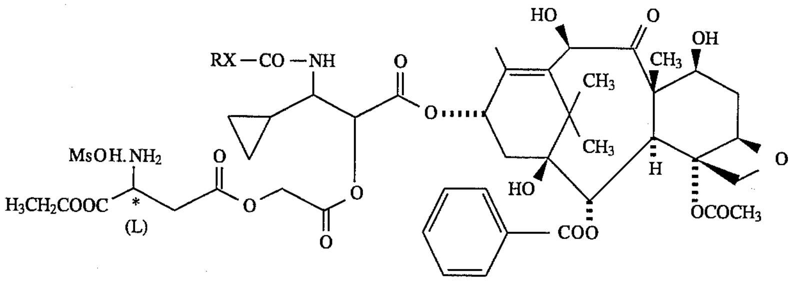

| Example No. | RX | Physical properties |
|---|---|---|
| 8 | 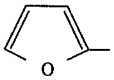 | FAB-MS(m/z): 967($MH^+$)<br>IR(nujol, $cm^{-1}$): 3400, 1750, 1650<br>NMR(DMSO-$d_6$, δ): 0.13–0.39(2H, m), 0.47–0.65(2H, m), 1.01(3H, s), 1.07(3H, s), 1.05–1.10(1H, m), 1.22(3H, t, J=7Hz), 1.55(3H, s), 1.62–1.73(1H, m), 1.81(3H, s), 2.05–2.40(3H, m), 2.31(3H, s), 2.36(3H, s), 2.95–3.16(2H, m), 3.76(1H, d, J=7Hz), 4.00–4.14(4H, m), 4.15–4.30(2H, m), 4.36–4.40(1H, m), 4.75(1H, s), 4.88(2H, s), 4.95(1H, m), 4.98(1H, s), 5.04(1H, d, J=7Hz), 5.13(1H, s), 5.26(1H, d, J=6Hz), 5.48(1H, d, J=7Hz), 5.98–6.05(1H, m), 6.64(1H, dd, J=2, 3Hz), 7.14(1H, dd, J=1, 3Hz), 7.49–7.70(3H, m), 7.86(1H, dd, J=1, 2Hz), 8.01(1H, d, J=7Hz), 8.28(3H, brs), 8.62(1H, d, J=9Hz) |
| 9 | $H_3C(CH_2)_3-O-$ | FAB-MS(m/z): 973($MH^+$)<br>IR(nujol, $cm^{-1}$): 3400–3360, 1750, 1710<br>NMR(DMSO-$d_6$, δ): 0.16(1H, m), 0.38(1H, m), 0.52(2H, m), 0.84(3H, t, J=7Hz), 1.01(3H, s), 1.04(3H, s), 1.09(1H, m), 1.23(3H, t, J=7Hz), 1.26(2H, m), 1.49(2H, m), 1.54(3H, s), 1.68(1H, m), 1.79(3H, s), 2.16(1H, m), 2.25(2H, m), 2.30(3H, s), 2.32(3H, s), 3.04(1H, dd, J=6, 17Hz), 3.11(1H, dd, J=6, 17Hz), 3.47(1H, m), 3.74(1H, d, J=7Hz), 3.92(2H, m), 4.06(3H, m), 4.22(2H, m), 4.41(1H, t, J=6Hz), 4.69(1H, s, $D_2O$exch.), 4.89(2H, s), 4.94(1H, m), 4.99(1H, brs, $D_2O$exch.), 5.04(1H, d, J=7Hz, $D_2O$exch.), 5.13(2H, m), 5.46(1H, d, J=7Hz), 6.00(1H, m), 7.49(1H, d, J=9Hz), 7.55(2H, m), 7.67(1H, m), 8.02(2H, m), 8.42(3H, brs, $D_2O$exch.) |

TABLE 9

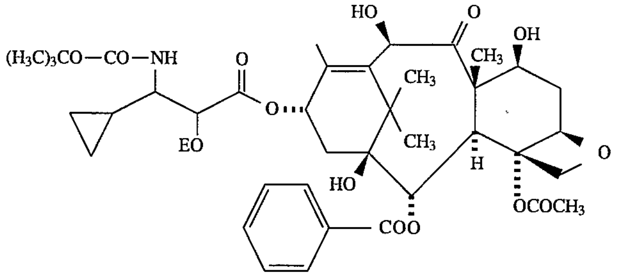

| Example No. | E | Physical properties |
|---|---|---|
| 10 | 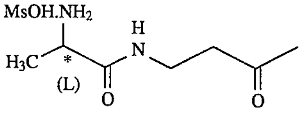 | FAB-MS(m/z): 914(MH$^+$)<br>IR(nujol, cm$^{-1}$): 3400, 1740, 1705<br>NMR(DMSO-$d_6$, δ): 0.12–0.18(1H, m), 0.33–0.39(1H, m), 0.48–0.55(2H, m), 1.02(3H, s), 1.03(3H, s), 1.03–1.10(1H, m), 1.33(1H, d, J=9Hz), 1.34(9H, s), 1.54(3H, s), 1.65–1.70(1H, m), 1.81(3H, s), 2.19–2.37 (3H, m), 2.31(3H, s), 2.32(3H, s), 2.64–2.70 (2H, m), 3.34–3.49(3H, m), 3.74(1H, d, J=7Hz), 3.78–3.81(1H, m), 4.01–4.09(3H, m), 4.65(1H, s), 4.93–5.10(4H, m), 5.14(1H, s), 5.47(1H, d, J=7Hz), 5.93–5.98(1H, m), 7.19(1H, d, J=9Hz), 7.54–7.58(2H, m), 7.63–7.69(1H, m), 7.95–8.10(5H, m), 8.48(1H, t, J=5Hz) |

TABLE 10

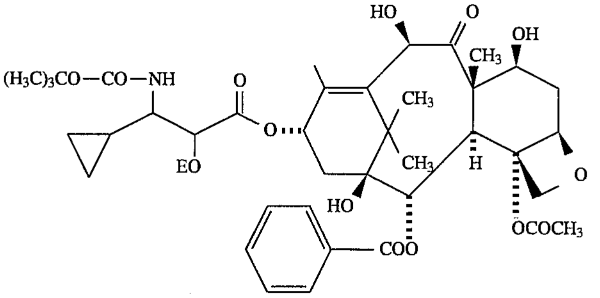

| Example No. | E | Physical properties |
|---|---|---|
| 11 | 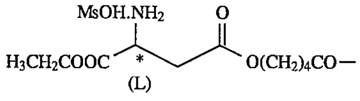 | FAB-MS(m/z): 1015(MH$^+$)<br>IR(nujol, cm$^{-1}$): 3380, 1740, 1710<br>NMR(DMSO-$d_6$, δ): 0.12–0.14(1H, m), 0.34–0.37(1H, m), 0.51–0.54(2H, m), 1.02(3H, s), 1.03(3H, s), 1.02–1.11(1H, m), 1.22(3H, t, J=7Hz), 1.35(9H, s), 1.54(3H, s), 1.65–1.71(5H, m), 1.80(3H, s), 2.18–2.29 (2H, m), 2.30(3H, s), 2.33(3H, s), 2.47–2.51(3H, m), 2.88(1H, dd, J=5, 17Hz), 2.98(1H, dd, J=6, 17Hz), 3.42(1H, m), 3.75(1H, d, J=7Hz,), 4.04–4.10(5H, m), 4.17–4.24(2H, m), 4.36(1H, t, J=6Hz), 4.66(1H, s), 4.94–4.97(2H, m), 5.05(1H, d, J=7Hz), 5.14(1H, s), 5.47(1H, d, J=7Hz), 5.95(1H, t, J=9Hz), 7.17(1H, d, J=9Hz), 7.56(2H, t, J=8Hz), 7.67(1H, t, J=7Hz), 8.01(2H, d, J=7Hz), 8.33(3H, brs) |

TABLE 11

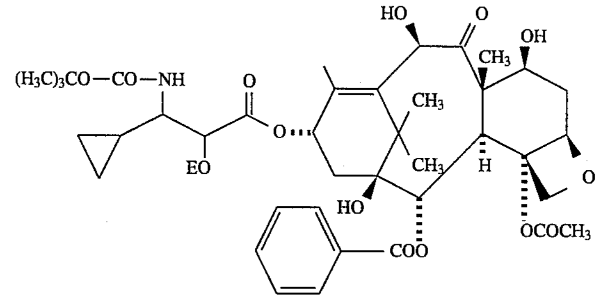

| Example No. | E | Physical properties |
|---|---|---|
| 12 | 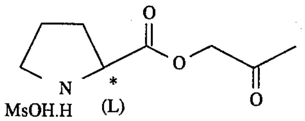 | FAB-MS(m/z): 927(MH+)<br>IR(nujol, $cm^{-1}$): 3370, 1750, 1710<br>NMR(DMSO-$d_6$, δ): 0.15(1H, m), 0.38(1H, m), 0.53(2H, m), 1.02(3H, s), 1.03(3H, s), 1.0–1.1(1H, m), 1.35(9H, s), 1.54(3H, s), 1.68(1H, m), 1.78(3H, s), 1.95(2H, m), 2.10(1H, m), 2.2–2.4(4H, m), 2.31(3H, s), 2.32(3H, s), 3.26(2H, m), 3.39(1H, m), 3.74(1H, d, J=7Hz), 4.06(3H, m), 4.59(1H, dd, J=7, 8Hz), 4.68(1H, s), 4.9–5.1(6H, m), 5.13(1H, s), 5.47(1H, d, J=7Hz), 5.95(1H, m), 7.22(1H, d, J=9Hz, $D_2O$exch.), 7.56(2H, m), 7.67(1H, m), 8.01(2H, m), 9.24(2H, brs, $D_2O$exch.) |

Example 13–14

The corresponding starting compounds are treated in the same manner as described in Example 1(1)–(11) and 2 to give the compounds shown in Tables 12.

TABLE 12

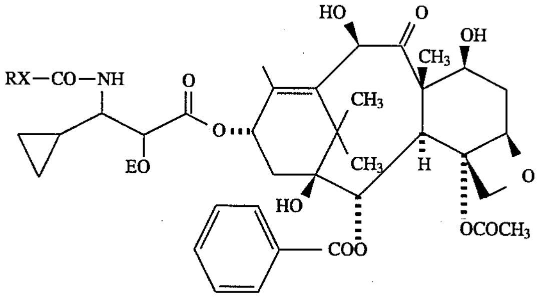

| Example No. | RX | E | Physical properties |
|---|---|---|---|
| 13 | 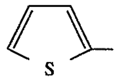 | H | FAB-MS(m/z): 782(MH+)<br>IR(nujol, $cm^{-1}$): 3460, 3400, 3260, 1740, 1720, 1700, 1690, 1645<br>NMR($CDCl_3$, δ): 0.36–0.72(4H, m), 1.11(3H, s), 1.20(3H, s), 1.35–1.45(1H, m), 1.76(3H, s), 1.79–1.91(1H, m), 1.89(3H, d, J=1Hz), 2.30(2H, m), 2.42(3H, s), 2.52–2.65(1H, m), 3.82(1H, dt, J=2, 9Hz), 3.86(1H, d, J=5Hz), 3.90(1H, d, J=7Hz), 4.16–4.29(3H, m), 4.32(1H, d, J=9Hz), 4.54(1H, dd, J=2, 5Hz), 4.96(1H, dd, J=2, 9Hz), 5.20(1H, d, J=2Hz), 5.68(1H, d, J=7Hz), 6.20(1H, m), 6.47(1H, d, J=9Hz), 7.0–8.15(8H, m) |

TABLE 12-continued

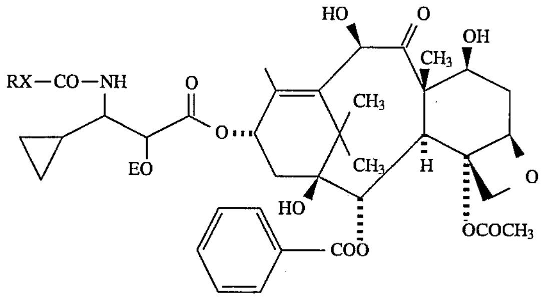

| Example No. | RX | E | Physical properties |
|---|---|---|---|
| 14 | $(H_3C)_3CS-$ | H | FAB-MS(m/z): 788(MH+)<br>IR(nujol, $cm^{-1}$): 3420, 1730, 1660<br>NMR($CDCl_3$, δ): 0.25–0.5(4H, m),<br>1.12(3H, s), 1.23(3H, s), 1.2–1.3(1H, m),<br>1.36(9H, s), 1.75(3H, s), 1.79–1.91(1H, m),<br>1.93(3H, d, J=1Hz), 2.30(2H, d, J=9Hz),<br>2.32(3H, s), 2.52–2.65(1H, m),<br>3.55(1H, bs), 3.61(1H, dt, J=2, 9Hz),<br>3.91(1H, d, J=7Hz), 4.16–4.29(3H, m),<br>4.33(1H, d, J=8Hz), 4.42(1H, dd, J=2, 5Hz),<br>4.97(1H, dd, J=2,9Hz), 5.24(1H, d, J=2Hz),<br>5.68(1H, d, J=9Hz), 5.69(1H, d, J=7Hz),<br>6.20(1H, m), 7.47–8.15(5H, m) |

Example 15–20

The corresponding starting compounds are treated in the same manner described in Example 1 or 4–7 to give the compounds shown in Tables 13–18.

TABLE 13

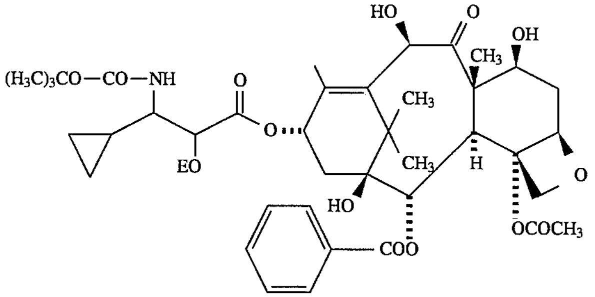

| Example No. | E | Physical properties |
|---|---|---|
| 15 | 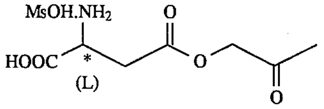 | FAB-MS(m/z): 967(M+Na+)<br>IR(nujol, $cm^{-1}$): 3400, 1745, 1710<br>NMR(DMSO-$d_6$, δ): 0.13–0.15(1H, m),<br>0.34–0.38(1H, m), 0.51–0.53(2H, m), 0.98–1.06(1H, m), 1.02(3H, s), 1.03(3H, s),<br>1.34(9H, s), 1.54(3H, s), 1.64–1.72(1H, m),<br>1.79(3H, s), 2.22–2.27(3H, m), 2.29(3H, s),<br>2.32(3H, s), 2.97–3.09(2H, m), 3.32–3.45(1H, m), 3.74(1H, d, J=7Hz),<br>4.04(1H, d, J=8Hz), 4.08(1H, d, J=8Hz),<br>4.03–4.09(1H, m), 4.24(1H, m), 4.66(1H, s),<br>4.89(2H, s), 4.93–4.98(2H, m), 5.04–5.07(1H, m), 5.14(1H, s),<br>5.47(1H, d, J=7Hz), 5.92–5.97(1H, m),<br>7.21(1H, d, J=9Hz), 7.56(2H, t, J=8Hz),<br>7.67(1H, t, J=7Hz), 8.01(2H, d, J=7Hz),<br>7.97–8.01(1H, m), 8.28(3H, br) |

TABLE 14

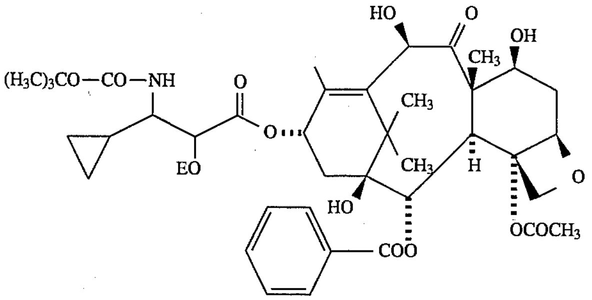

| Example No. | E | Physical properties |
|---|---|---|
| 16 | 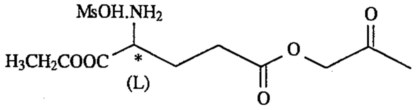 | FAB-MS(m/z): 987($MH^+$), 1009($M^+$+Na) IR(nujol, $cm^{-1}$): 3400, 1745, 1710 NMR(DMSO-$d_6$, δ): 0.15(1H, m), 0.36(1H, m), 0.52(2H, m), 1.02(3H, s), 1.03(3H, s), 1.0–1.1 (1H, m), 1.25(3H, t, J=7Hz), 1.35(9H, s), 1.54(3H, s), 1.68(1H, m), 1.78(3H, s), 2.07(2H, m), 2.2–2.3(3H, m), 2.30(3H, s), 2.32(3H, s), 2.66(2H, m), 3.40(1H, m), 3.74(1H, d, J=7Hz), 4.07(4H, m), 4.23(2H, q, J=7Hz), 4.66(1H, s, $D_2O$exch.), 4.85(2H, s), 4.95(1H, m), 4.97(1H, d, J=2Hz, $D_2O$exch.), 5.05(2H, m), 5.13(1H, d, J=2Hz), 5.47(1H, d, J=7Hz), 5.95(1H, m), 7.21(1H, d, J=9Hz), 7.56(2H, m), 7.66(1H, m), 8.02(2H, m), 8.30(3H, brs, $D_2O$exch.) |

TABLE 15

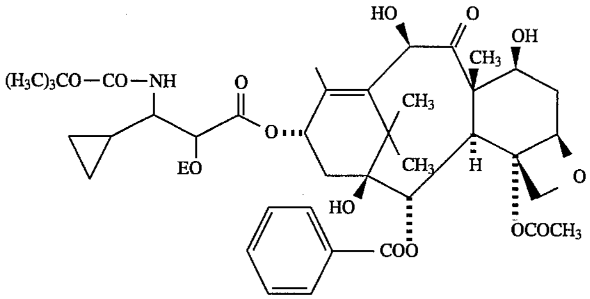

| Example No. | E | Physical properties |
|---|---|---|
| 17 | 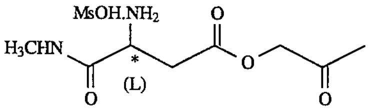 | FAB-MS(m/z): 958($MH^+$), 980($M^+$+Na) IR(nujol, $cm^{-1}$): 3380, 1740, 1705 NMR(DMSO-$d_6$, δ): 0.13(1H, m), 0.37(1H, m), 0.52(2H, m), 1.02(3H, s), 1.03(3H, s), 1.1–1.0(1H, m), 1.34(9H, s), 1.54(3H, s), 1.68(1H, m), 1.78(3H, s), 2.2–2.3(3H, m), 2.30(3H, s), 2.32(3H, s), 2.67(3H, d, J=5Hz), 2.92(1H, dd, J=7, 17Hz), 3.04(1H, dd, J=5, 17Hz), 3.41(1H, m), 3.74(1H, d, J=7Hz), 4.07(4H, m), 4.66(1H, s, $D_2O$exch.), 4.89(2H, s), 4.96(2H, m), 5.05(2H, m), 5.14(1H, d, J=2Hz), 5.47(1H, d, J=7Hz), 5.95(1H, m), 7.21(1H, d, J=9Hz), 7.56(2H, m), 7.67(1H, m), 8.02(2H, m), 8.16(3H, brs, $D_2O$exch.), 8.39(1H, m, $D_2O$exch.) |

TABLE 16
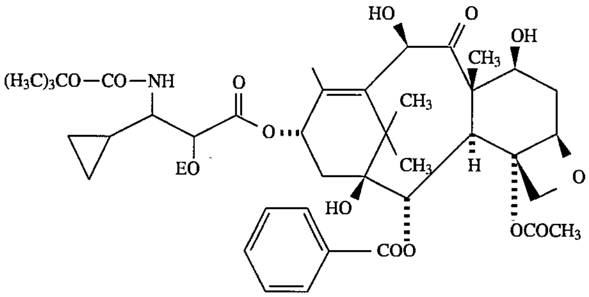
| Example No. | E | Physical properties |
|---|---|---|
| 18 | 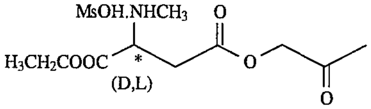 | FAB-MS(m/z): 1009($M^+$+Na), 987($M^+$+H)<br>IR(nujol, $cm^{-1}$): 3395, 1745, 1707<br>NMR(DMSO-$d_6$, δ): 0.11–0.18(1H, m), 0.34–0.40(1H, m), 0.49–0.55(2H, m), 1.00–1.06(1H, m), 1.02(3H, s), 1.03(3H, s), 1.24(6H, t, J=7.0Hz), 1.35(9H, s), 1.55(3H, s), 1.63–1.74(1H, m), 1.78(3H, s), 2.20–2.30(3H, m), 2.30(3H, s), 2.31(3H, s), 2.65(3H, s), 3.13–3.26(2H, m), 3.35–3.45(1H, m), 3.74(1H, d, J=7.0Hz), 4.03–4.11(3H, m), 4.19–4.29(2H, m), 4.43(1H, brt, J=5Hz), 4.65(1H, brs), 4.90(2H, s), 4.93–4.97(1H, m), 5.00–5.05(1H, m), 5.06(1H, d, J=4Hz), 5.14(1H, s), 5.47(1H, d, J=7Hz), 5.91–5.99(1H, m), 7.19(1H, m), 7.53–7.70(3H, m),<br>8.02(2H, d, J=7Hz), 9.07(1H, brs) |

TABLE 17
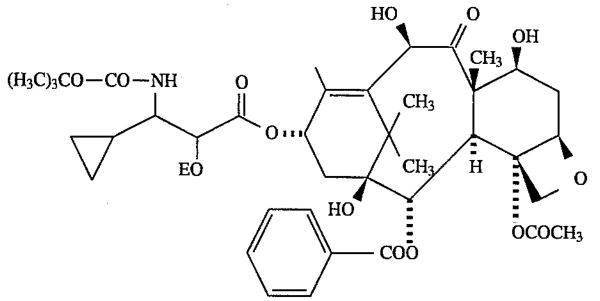
| Example No. | E | Physical properties |
|---|---|---|
| 19 | 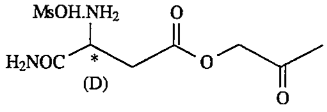 | FAB-MS(m/z): 966(M+Na)+<br>IR(nujol, $cm^{-1}$): 3400, 1740, 1705<br>NMR(DMSO-$d_6$, δ): 0.13–0.19(1H, m), 0.35–0.41(1H, m), 0.49–0.56(2H, m), 0.97–1.10(1H, m), 1.02(3H, s), 1.03(3H, s), 1.35(9H, s), 1.54(3H, s), 1.62–1.75(1H, m), 1.79(3H, s), 2.09–2.40(3H, m), 2.30(3H, s), 2.31(3H, s), 2.95(1H, dd, J=8, 18Hz), 3.08(1H, dd, J=5, 18Hz), 3.34–3.45(1H, m), 3.74(1H, d, J=7Hz), 4.01–4.10(4H, m), 4.66(1H, brs), 4.85–5.15(2H, br), 4.90(2H, s), 4.95(1H, dlike, J=11Hz), 5.06(1H, d, J=5Hz), 5.14(1H, s), 5.47(1H, d, J=7Hz), 5.92–5.96(1H, m), 7.21(1H, d, J=9Hz), 7.56(2H, tlike, J=7Hz), 7.67(1H, tlike, J=7Hz), 7.69(1H, s), 7.90(1H, s), 8.01(2H, dlike, J=7Hz), 8.18(3H, brs) |

TABLE 18

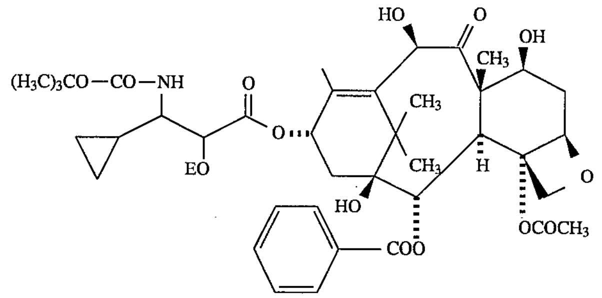

| Example No. | E | Physical properties |
| --- | --- | --- |
| 20 | 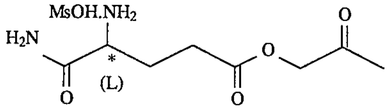 | LC-MS(m/z): 958(MH+)<br>IR(nujol, cm−1): 3400, 1745, 1707<br>NMR(DMSO-$d_6$, δ): 0.15(1H, m), 0.37(1H, m), 0.52(2H, m), 0.95–1.10(1H, m), 1.02(3H, s), 1.03(3H, s), 1.35(9H, s), 1.54(3H, s), 1.68(1H, m), 1.78(3H, s), 2.03(2H, m), 2.17–2.34 (3H, m), 2.30(3H, s), 2.32(3H, s), 2.95(1H, dd, J=8, 17Hz), 3.08(1H, dd, J=5, 17Hz), 3.41(1H, m), 3.74(1H, d, J=7Hz), 4.06(4H, m), 4.67(1H, s, $D_2O$exch.), 4.89(2H, s), 4.95(1H, d, J=11Hz), 4.98(1H, d, J=2Hz, $D_2O$exch.), 5.05(1H, d, J=7Hz), 5.07(1H, d, J=4Hz), 5.14(1H, d, J=2Hz), 5.47(1H, d, J=7Hz), 5.95(1H, m), 7.21(1H, d, J=9Hz), 7.56(2H, t, J=8Hz), 7.64(1H, s, $D_2O$exch.), 7.67(1H, m), 7.87(1H, s, $D_2O$exch.), 8.02(2H, d, J=7Hz), 8.09(3H, brs, $D_2O$exch.) |

Example 21–24

The corresponding starting compounds are treated in the same manner as described in Example 1 or 4–7 to give the compounds shown in Tables 19.

TABLE 19

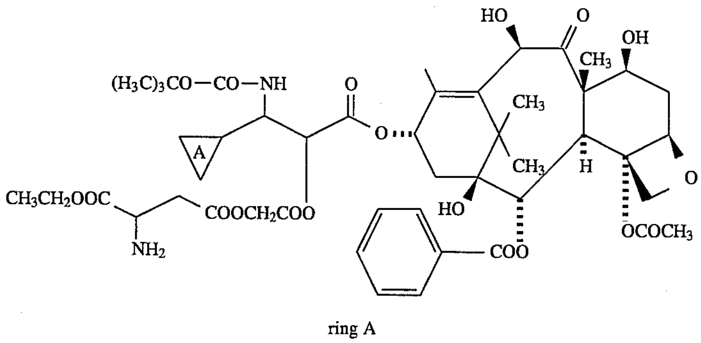

| Example No. | ring A |
| --- | --- |
| 21 | 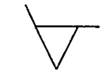 |
| 22 | 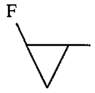 |

TABLE 19-continued

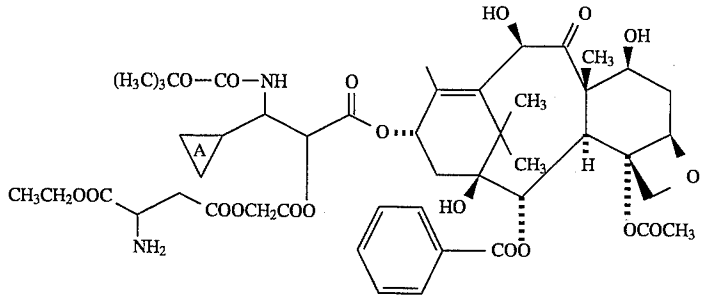

| Example No. | ring A |
| --- | --- |
| 23 | 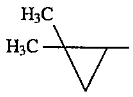 |
| 24 | 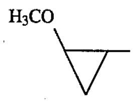 |

Example 25

(1) To 13.13 g of (1R,2R)-2-methylcyclopropyl-1,2-bis(isopropyloxycarbonyl)methylene acetal in a mixture of 40 ml of tetrahydrofuran and 80 ml of water is added 9.15 g of p-toluenesulfonic acid monohydrate. The reaction mixture is refluxed under heating for 8 hours. After the reaction mixture is cooled, a saturated aqueous solution of sodium hydrogen carbonate and 400 ml of toluene are added to the mixture. The aqueous layer is extracted with toluene twice. After the organic layer is dried over sodium sulfate, inorganic materials are removed by filtration. A 27.09 g of benzyloxycarbonylmethylenetriphenylphosphorane is added to the solution. The mixture is stirred at 80° C. for 18 hours. The solvent is removed in vacuo and the residue is purified by silica gel column chromatography (solvent;hexane:ethyl acetate=15:1) to give 6.67 g of benzyl trans-3-(2-methyl)cyclopropylacrylate. Benzyl trans-3-(2-methyl)cyclopropylacrylate is treated in the same manner as described in Example 1 (2)-(8) to give (4S,5R)-3-tert-butoxycarbonyl-2,2-dimethyl-4-[(1R,2R)-2-methyl]cyclopropyl-5-oxazolidinecarboxylic acid.

m.p.: 86°–91° C. FAB-MS(m/z): 300($MH^+$)

(2)(4S ,5R)-3-tert- Butoxycarbonyl-2,2-dimethyl-4-[(1R, 2R)-2methyl]cyclopropyl-5-oxazolidinecarboxylic acid and 4α-acetoxy-2α-benzoyloxy-5β, 20-epoxy-1β,13α-dihydroxy-7β,10β-bis(2,2,2-trichloroethoxycarbonyloxy)tax-11-en-9-one are treated in the same manner as described in Example 1 (9) to give 4α-acetoxy-2α-benzoyloxy-13α-{(4S,5R)-3-tert-butoxycarbonyl-2,2-dimethyl-4-[(1R,2R)-2-methyl]cyclohexyloxazolidin-5-ylcarbonyloxy}-5β,20epoxy-1β-hydroxy-7β,10β-bis(2,2,2-trichloroethoxycarbonyloxy)tax-11-en-9-one. FAB-MS(m/z): 1198($M^+$+Na)

(3) 4α-Acetoxy-2α-benzoyloxy-13α-{(4S,5R)-3-tert-butoxycarbonyl-2,2-dimethyl-4-[(1R,2R)-2-methyl]cyclohexyloxazolidin-5-ylcarbonyloxy}-5β,20epoxy-1β-hydroxy-7β,10β-bis(2,2,2-trichloroethoxycarbonyloxy)tax-11-en-9-one is treated in the same manner as described in Example 2 to give 4α-acetoxy-2α-benzoyloxy-13α-{(2R,3S)-3-tert-butoxycarbonylamino-2-hydroxy-3-[(1R,2R)-2-methyl]cyclopropylpropionyloxy}-5β,20epoxy-1β,7β,10β,10β-trihydroxytax-11-en-9-one.

m.p.: 167°–174° C. FAB-MS(m/z): 808($M^+$+Na)

(4) 4α-Acetoxy-2α-benzoyloxy-13α-{(2R,3S)-3-tert-butoxycarbonylamino-2-hydroxy-3-[(1R,2R)-2-methyl]cyclopropylpropionyloxy}-5β,20epoxy-1β,7β,10β-trihydroxytax-11-en-9-one is treated in the same manner as described in Example 5 to give 4α-acetoxy-2α-benzoyloxy-13α-{(2R,3S)-3-tert-butoxycarbonylamino-2-[(3S)-3-amino-3-ethoxycarbonylpropionyloxyacetoxy ]-3-[(1R,2R)-2-methyl]cyclopropylpropionyloxy}-5β,20epoxy-1β,7β,10 β,10β-trihydroxytax-11-en-9-one methanesulfonate.

m.p.: >152° C. (decomposed) FAB-MS(m/z): 1009($M^+$+Na) IR(nujol,$cm^{-1}$): 3400,1750,1720

NMR(300MHz,DMSO-$d_6$, δ): 0.24–0.33(1H,m), 0.50–0.65(2H,m), 0.70–0.81(1H,m), 0.99(3H,d,J=6 Hz), 1.03(6H,s), 1.24(3H,t,J=7 Hz), 1.33(9H,s), 1.54(3H,s), 1.59–1.74(1H,m), 1.78(3H,s), 2.19–2.27(3H,m), 2.31 (6H, s), 3.08(1H,dd,J=6,18 Hz), 3.25–3.54(1H,m), 3.74(1H,d,J=7 Hz), 4.01–4.13(3H,m), 4.16–4.28(2H,m), 4.40(1H,t,J=6 Hz), 4.64(1H,s), 4.90(2H,s), 4.92–4.99(2H,m), 5.05(1H,d, J=8 Hz), 5.11 (1H,d,J=4 Hz), 5.14(1H,s), 5.47(1H,d,J=7 Hz), 5.89–6.00(1H,m), 7.15(1H,d,J=9 Hz), 7.51–7.59(2H, m), 7.64–7.72(1H,m), 8.02(2H,d-like,J=7 Hz), 8.37(3H,brs).

Example 26

4α-Acetoxy-2α-benzoyloxy-13α-{(4S,5R)-3-tert-butoxycarbonyl-2,2-dimethyl-4-[(1R,2R)-2-methyl]cyclohexyloxazolidin-5-ylcarbonyloxy}-5β,20epoxy-1β-hydroxy-7β,10β-bis(2,2,2-trichloroethoxycarbonyloxy)tax-11-en-9-one obtained in Example 25(2) is treated in the same manner as described in Example 1(10)–(14) to give 4α-acetoxy-2α-benzoyloxy-13α-{(2R,3S)-3-tert-butoxycarbonylamino-2-[(3S)-3-amino-3-ethoxycarbonylpropionyloxyacetoxy]-3-[(1R,2R)-2-methyl]cyclopropylpropionyloxy}-5β, 20-epoxy-1β,7β,10β,10β-trihydroxytax-11-en-9- one methanesulfonate. The physical properties of the product are the same as those of the compound of Example 25(4).

Reference Example

A solution of 3.29 g of 4α-acetoxy-2α-benzoyloxy-5β, 20epoxy-1β,10β, 13α-trihydroxy-7β-triethylsilyloxytax-11-en-9-one in 10 ml of pyridine is cooled in an ice-bath, and 1.38 ml of trichloroethylformic acid chloride is added dropwise thereto. The mixture is warmed to room temperature and stirred for 7 hours. The reaction mixture is extracted with ethyl acetate by pouring into a mixture of ethyl acetate and ice- water. The extract is washed with water and brine, dried over magnesium sulfate and evaporated to remove the solvent. The residue is purified by silica gel column chromatography (solvent; toluene:ethyl acetate=4:1) to give 4α-acetoxy-2α-benzoyloxy-5β,20epoxy-1β-hydroxy-7β-triethylsilyloxy-10β-(2,2,2-trichloroethoxycarbonyloxy)tax-11-en-9-one.

Yield: 74% FAB-MS(m/z): 835($MH^+$) IR(nujol,$cm^{-1}$): 3470,1770,1725,1710

NMR($CDCl_3$, δ): 0.58(6H,q,J=7 Hz), 0.93(9H,t,J=7 Hz), 1.64(3H,s), 1.85–1.92(1H,m), 2.08(1H,d,J=5 Hz), 2.20(3H, s), 2.29(3H,s), 2.20–2.30(2H,m), 2.50–2.58(1H,m), 3.84(1H,d,J=7 Hz), 4.15(1H,d,J=8 Hz), 4.31 (1H,d,J=8 Hz), 4.47–4.51(1H,m), 4.79(1H,d,J=12 Hz), 4.83(1H,d,J=12 Hz), 4.83–4.88(1H,m), 4.96(1H,d, J=8 Hz), 5.64(1H,d,J=7 Hz), 6.30(1H,s), 7.26–7.63(3H,m), 8.10(2H,d,J=7 Hz)

Effects of the Invention

The compound [I] or a pharmaceutically acceptable salt thereof in the present invention has high water-solubility, high stability, and also an excellent antitumor activity. For example, the taxol derivative in the present invention exhibits excellent antitumor activities and life-prolongating effects on mice to which P-388 cells are transplanted intraperitoneally, nude mice to which human breast carcinoma MX-1 cells are transplanted subcutaneously, or mice to which B16 melanoma cells are transplanted intraperitoneally or subcutaneously.

Further, the taxol derivative or a pharmaceutically acceptable salt thereof in the present invention has low toxicity. For example, when 4α-acetoxy-13α-{(2R,3S)-3-tert-butoxycarbonylamino-2-[((3S)-3-amino-3-ethoxycarbonylpropionyloxy)acetoxy]-3-cyclopropylpropionyloxy}-2α-benzoyloxy-5β, 20-epoxy-1β,7β,10β-trihydroxytax-11-en-9-one methanesulfonate is intravenously administered (25 mg/kg) for 5 days once a day to $BDF_1$ mice to which B16 melanoma cells transplanted subcutaneously, no death of mice is observed in more than 30 days.

Thus, the compound [I] in the present invention can be suitably used for medical treatment of a wide range of tumors such as breast cancer, ovary cancer, lung cancer, malignant melanoma, and the like.

What is claimed is:

1. A compound represented by the formula [IX]:

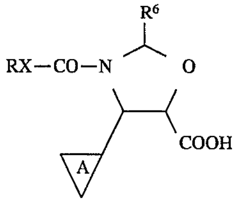

[IX]

wherein ring A represents a substituted or unsubstituted cyclopropane ring; $R^6$ represents a substituted phenyl group; X represents a single bond or a group represented by —O—, —S— or —NH—; and R represents a substituted or unsubstituted lower alkyl group (wherein said lower alkyl group may have a cycloalkyl moiety), a substituted or unsubstituted aryl group, or a substituted or unsubstituted aromatic heterocyclic group or a reactive derivative thereof.

2. A compound represented by the formula [XI]:

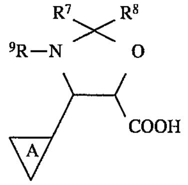

[XI]

wherein ring A represents a substituted or unsubstituted cyclopropane ring; $R^7$ and $R^8$ represent lower alkyl groups; and $R^9$ represents a protecting group or a reactive derivative thereof.

* * * * *